(12) United States Patent
Savitzky et al.

(10) Patent No.: US 6,740,516 B2
(45) Date of Patent: May 25, 2004

(54) NUCLEIC ACID AND AMINO ACID SEQUENCES

(75) Inventors: Kinneret Savitzky, Tel Aviv (IL); Liat Mintz, Ramat Hasharon (IL); Anat David, Givataim (IL); Idit Azar, Rehovot (IL)

(73) Assignee: Compugen Ltd., Tel Aviv (IL)

( * ) Notice: Subject to any disclaimer, the term of this patent is extended or adjusted under 35 U.S.C. 154(b) by 0 days.

(21) Appl. No.: 09/755,100

(22) Filed: Jan. 8, 2001

(65) Prior Publication Data

US 2002/0099189 A1 Jul. 25, 2002

Related U.S. Application Data

(63) Continuation-in-part of application No. 09/701,238, filed as application No. PCT/IL00/00102 on Feb. 18, 2000, now abandoned.

(30) Foreign Application Priority Data

Feb. 18, 1999 (IL) ................................................. 128587
Apr. 14, 1999 (IL) ................................................. 129439
Aug. 11, 1999 (IL) ................................................. 131363

(51) Int. Cl.⁷ ................................................. C12H 1/20
(52) U.S. Cl. ................ 435/252.3; 435/69.1; 435/320.1; 435/325; 536/23.5
(58) Field of Search ....................... 536/23.5; 435/69.1, 435/325, 252.3, 320.1

(56) References Cited

U.S. PATENT DOCUMENTS 4,889,806 A * 12/1989 Olson et al. ............. 435/172.3
5,585,479 A * 12/1996 Hoke et al. ................ 536/24.5
6,303,361 B1 * 10/2001 Vihko ........................ 435/226

FOREIGN PATENT DOCUMENTS

WO   WO 9212430   7/1992
WO   WO 9846795   10/1998

OTHER PUBLICATIONS

Tao et al, 1989, J Immunol, 143(8): 2595–2601.*
Burgess et al, 1990, J Cell Biol, 111: 2129–2138.*
Lazar et al, 1988, Mol Cell Biol, 8: 1247–1252.*
Gillies et al, 1990, Human Antibodies Hybridoma, 1(1): 47–54.*
Jansen et al, 1995, Pediatric Res, 37(6): 681–686.*
Alberts et al, 1994, Mol Biol Cell, 3rd ed, p. 465.*
Shantz, 1999, Int J Biochem cell Biol, 31: 107–122.*
McClean et al, 1993, Eur J Cancer, 29A: 2243–2248.*
Fu et al, 1996, EMBO J, 15: 4392–4401.*
Yokota et al, 1988, Oncogene, 3: 471–475.*
Gura, 1997, Science, 278: 1041–1042.*
Jain, 1994, Sci Amer, 271: 58–65.*
Curti, 1993, Crit rev Oncol/Hematol, 14: 29–39.*
Hartwell, 1997, Science, 278: 1064–1068.*
Gura, 1995, Science, 270: 575–577.*
Miller, 1995, FASEB J, 9: 190–199.*
Deonarain, 1998, Expert Opin Ther Pat, 8: 53–69.*
Verma, 1997, Nature, 389: 239–242.*
Crystal, 1995, Science, 270: 404–410.*
Schedlich et al, 1987, Genbank, Accession No: M18157, and MPSRCH search report, 2002, pp. 1–8 for SEQ ID No:6.*
MPSRCH search report, 2002, for SEQ ID No:12, p. 1.*
Johnstone et al, 1987, In. Immunochemistry in Practice, 2nd Ed., Blackwell Scientific Publ, Oxford, p. 49–50.*
Riegman et al.; Characterization of the Prostate . . . ; Biochemical and Biophysical Research Communications; vol. 159, No. 1, (1989); pp. 95–102.
Baffa et al.; A Comparative Analysis of Prostate . . . ; Urology; vol. 47, No. 6, (1996); pp. 795–800.
Riegman et al.; Identification and androgen–regulated . . . ; Molecular and Cellular Endocrinology, vol. 76, (1991); pp. 181–190.
Thiounn et al.; Positive Prostate–Specific . . . ; Urology; vol. 50, (1997); pp. 245–250.
Riegman et al.; Molecular Cloning and . . . Biochemical and Biophysical Research Communications, vol. 155, No. 1, (1988); pp. 181–188.

* cited by examiner

*Primary Examiner*—Anthony C. Caputa
*Assistant Examiner*—Minh-Tam Davis
(74) *Attorney, Agent, or Firm*—Finnegan, Henderson, Farabow, Garrett & Dunner

(57) ABSTRACT

An isolated nucleic acid sequence depicted in SEQ ID NO:6 is an alternative splice variant of human kallikrien-2 gene (KLK-2). An expression vector containing the splice variant and a host cell transfected by the expression vector are provided. The nucleic acid is useful for determining the level of nucleic acid sequences of human kallikrien variants in a biological sample.

6 Claims, 25 Drawing Sheets

```
   1  AAGCTTCTAG TTTTCTTTTC CCGGTGACAT CGTGGAAAGC ACTAGCATCT
  51  CTAAGCAATG ATCTGTGACA ATATTCACAG TGTAATGCCA TCCAGGGAAC
 101  TCAACTGAGC CTTGATGTCC AGAGATTTTT GTGTTTTTT CTGAGACTGA
 151  GTCTCGCTCT GTGCCAGGCT GGAGTGCAGT GGTGCAACCT TGGCTCACTG
 201  CAAGCTCCGC CTCCTGGGTT CACGCCATTC TCCTGCCTCA GCCTCCTGAG
 251  TAGCTGGGAC TACAGGCACC CGCCACCACG CCTGGCTAAT TTTTTTGTAT
 301  TTTTAGTAGA GATGGGGTTT CACTGTGTTA GCCAGGATGG TCTCAGTCTC
 351  CTGACCTCGT GATCTGCCCA CCTTGGCCTC CCAAAGTGCT GGGATGACAG
 401  GCGTGAGCCA CCGCGCCTGG CCGATATCCA GAGATTTTTT GGGGGGCTCC
 451  ATCACACAGA CATGTTGACT GTCTTCATGG TTGACTTTTA GTATCCAGCC
 501  CCTCTAGAAA TCTAGCTGAT ATAGTGTGGC TCAAAACCTT CAGCACAAAT
 551  CACACCGTTA GACTATCTGG TGTGGCCCAA ACCTTCAGGT GAACAAAGGG
 601  ACTCTAATCT GGCAGGATAT TCCAAAGCAT TAGAGATGAC CTCTTGCAAA
 651  GAAAAAGAAA TGGAAAAGAA AAAGAAAGAA AGGAAAAAAA AAAAAAAAA
 701  GAGATGACCT CTCAGGCTCT GAGGGAAAC GCCTGAGGTC TTTGAGCAAG
 751  GTCAGTCCTC TGTTGCACAG TCTCCCTCAC AGGGTCATTG TGACGATCAA
 801  ATGTGGTCAC GTGTATGAGG CACCAGCACA TGCCTGGCTC TGGGGAGTGC
 851  CGTGTAAGTG TATGCTTGCA CTGCTGAATG CTTGGGATGT GTCAGGGATT
 901  ATCTTCAGCA CTTACAGATG CTCATCTCAT CCTCACAGCA TCACTATGGG
 951  ATGGGTATTA CTGGCCTCAT TTGATGGAGA AAGTGGCTGT GGCTCAGAAA
1001  GGGGGGACCA CTAGACCAGG GACACTCTGG ATGCTGGGA CTCCAGAGAC
1051  CATGACCACT CACCAACTGC AGAGAAATTA ATTGTGGCCT GATGTCCCTG
1101  TCCTGGAGAG GGTGGAGGTG GACCTTCACT AACCTCCTAC CTTGACCCTC
```

Fig.1

```
1151  TCTTTTAGGG CTCTTTCTGA CCTCCACCAT GGTACTAGGA CCCCATTGTA
1201  TTCTGTACCC TCTTGACTCT ATGACCCCCA CTGCCCACTG CATCCAGCTG
1251  GGTCCCCTCC TATCTCTATT CCCAGCTGGC CAGTGCAGTC TCAGTGCCCA
1301  CCTGTTTGTC AGTAACTCTG AAGGGGCTGA CATTTTACTG ACTTGCAAAC
1351  AAATAAGCTA ACTTTCCAGA GTTTTGTGAA TGCTGGCAGA GTCCATGAGA
1401  CTCCTGAGTC AGAGGCAAAG GCTTTTACTG CTCACAGCTT AGCAGACAGC
1451  ATGAGGTTCA TGTTCACATT AGTACACCTT GCCCCCCCCA AATCTTGTAG
1501  GGTGACCAGA GCAGTCTAGG TGGATGCTGT GCAGAAGGGG TTTGTGCCAC
1551  TGGTGAGAAA CCTGAGATTA GGAATCCTCA ATCTTATACT GGGACAACTT
1601  GCAAACCTGC TCAGCCTTTG TCTCTGATGA AGATATTATC TTCATGATCT
1651  TGGATTGAAA ACAGACCTAC TCTGGAGGAA CATATTGTAT CGATTGTCCT
1701  TGACAGTAAA CAAATCTGTT GTAAGAGACA TTATCTTTAT TATCTAGGAC
1751  AGTAAGCAAG CCTGGATCTG AGAGAGATAT CATCTTGCAA GGATGCCTGC
1801  TTTACAAACA TCCTTGAAAC AACAATCCAG AAAAAAAAG GTGTTGCTGT
1851  CTTTGCTCAG AAGACACACA GATACGTGAC AGAACCATGG AGAATTGCCT
1901  CCCAACGCTG TTCAGCCAGA GCCTTCCACC CTTGTCTGCA GGACAGTCTC
1951  AACGTTCCAC CATTAAATAC TTCTTCTATC ACATCCTGCT TCTTTATGCC
2001  TAACCAAGGT TCTAGGTCCC GATCGACTGT GTCTGGCAGC ACTCCACTGC
2051  CAAACCCAGA ATAAGGCAGC GCTCAGGATC CCGAAGGGGC ATGGCTGGGG
2101  ATCAGAACTT CTGGGTTTGA GTGAGGAGTG GGTCCACCCT CTTGAATTTC
2151  AAAGGAGGAA GAGGCTGGAT GTGAAGGTAC TGGGGGAGGG AAAGTGTCAG
2201  TTCCGAACTC TTAGGTCAAT GAGGGAGGAG ACTGGTAAGG TCCCAGCTCC
2251  CGAGGTACTG ATGTGGGAAT GGCCTAAGAA TCTCATATCC TCAGGAAGAA
2301  GGTGCTGGAA TCCTGAGGGG TAGAGTTCTG GGTATATTTG TGGCTTAAGG
```
Fig.1(Cont.)

2351 CTCTTTGGCC CCTGAAGGCA GAGGCTGGAA CCATTAGGTC CAGGGTTTGG

2401 GGTGATAGTA ATGGGATCTC TTGATTCCTC AAGAGTCTGA GGATCGAGGG

2451 TTGCCCATTC TTCCATCTTG CCACCTAATC CTTACTCCAC TTGAGGGTAT

2501 CACCAGCCCT TCTAGCTCCA TGAAGGTCCC CTGGGCAAGC ACAATCTGAG

2551 CATGAAAGAT GCCCCAGAGG CCTTGGGTGT CATCCACTCA TCATCCAGCA

2601 TCACACTCTG AGGGTGTGGC CAGCACCATG ACGTCATGTT GCTGTGACTA

2651 TCCCTGCAGC GTGCCTCTCC AGCCACCTGC CAACCGTAGA GCTGCCCATC

2701 CTCCTCTGGT GGGAGTGGCC TGCATGGTGC CAGGCTGAGG CCTAGTGTCA

2751 GACAGGGAGC CTGGAATCAT AGGGATCCAG GACTCAAAAG TGCTAGAGAA

2801 TGGCCATATG TCACCATCCA TGAAATCTCA AGGGCTTCTG GGTGGAGGGC

2851 ACAGGGACCT GAACTTATGG TTTCCCAAGT CTATTGCTCT CCCAAGTGAG

2901 TCTCCCAGAT ACGAGGCACT GTGCCAGCAT CAGCCTTATC TCCACCACAT

2951 CTTGTAAAAG GACTACCCAG GGCCCTGATG AACACCATGG TGTGTACAGG

3001 AGTAGGGGGT GGAGGCACGG ACTCCTGTGA GGTCACAGCC AAGGGAGCAT

3051 CATCATGGGT GGGGAGGAGG CAATGGACAG GCTTGAGAAC GGGGATGTGG

3101 TTGTATTTGG TTTTCTTTGG TTAGATAAAG TGCTGGGTAT AGGATTGAGA

3151 GTGGAGTATG AAGACCAGTT AGGATGGAGG ATCAGATTGG AGTTGGGTTA

3201 GATAAAGTGC TGGGTATAGG ATTGAGAGTG GAGTATGAAG ACCAGTTAGG

3251 ATGGAGGATC AGATTGGAGT TGGGTTAGAG ATGGGGTAAA ATTGTGCTCC

3301 GGATGAGTTT GGGATTGACA CTGTGGAGGT GGTTTGGGAT GGCATGGCTT

3351 TGGGATGGAA ATAGATTTGT TTTGATGTTG GCTCAGACAT CCTTGGGGAT

3401 TGAACTGGGG ATGAAGCTGG GTTTGATTTT GGAGGTAGAA GACGTGGAAG

3451 TAGCTGTCAG ATTTGACAGT GGCCATGAGT TTTGTTTGAT GGGGAATCAA

Fig.1(Cont.)

```
3501  ACAATGGGGG AAGACATAAG GGTTGGCTTG TTAGGTTAAG TTGCGTTGGG
3551  TTGATGGGGT CGGGGCTGTG TATAATGCAG TTGGATTGGT TTGTATTAAA
3601  TTGGGTTGGG TCAGGTTTTG GTTGAGGATG AGTTGAGGAT ATGCTTGGGG
3651  ACACCGGATC CATGAGGTTC TCACTGGAGT GGAGACAAAC TTCCTTTCCA
3701  GGATGAATCC AGGGAAGCCT TAATTCACGT GTAGGGAGG TCAGGCCACT
3751  GGCTAAGTAT ATCCTTCCAC TCCAGCTCTA AGATGGTCTT AAATTGTGAT
3801  TATCTATATC CACTTCTGTC TCCCTCACTG TGCTTGGAGT TTACCTGATC
3851  ACTCAACTAG AAACAGGGGA AGATTTTATC AAATTCTTTT TTTTTTTTT
3901  TTTTTTTTGA GACAGAGTCT CACTCTGTTG CCCAGGCTGG AGTGCAGTGG
3951  CGCAGTCTCG GCTCACTGCA ACCTCTGCCT CCCAGGTTCA AGTGATTCTC
4001  CTGCCTCAGC CTCCTGAGTT GCTGGGATTA CAGGCATGCA GCACCATGCC
4051  CAGCTAATTT TTGTATTTTT AGTAGAGATG GGGTTTCACC AATGTTGCC
4101  AGGCTGGCCT CGAACTCCTG ACCTGGTGAT CCACCTGCCT CAGCCTCCCA
4151  AAGTGCTGGG ATTACAGGCG TCAGCCACCG CGCCCAGCCA CTTTTGTCAA
4201  ATTCTTGAGA CACAGCTCGG GCTGGATCAA GTGAGCTACT CTGGTTTTAT
4251  TGAACAGCTG AAATAACCAA CTTTTTGGAA ATTGATGAAA TCTTACGGAG
4301  TTAACAGTGG AGGTACCAGG GCTCTTAAGA GTTCCCGATT CTCTTCTGAG
4351  ACTACAAATT GTGATTTGC ATGCCACCTT AATCTTTTT TTTTTTTTTT
4401  TAAATCGAGG TTTCAGTCTC ATTCTATTTC CCAGGCTGGA GTTCAATAGC
4451  GTGATCACAG CTCACTGTAG CCTTGAACTC CTGGCCTTAA GAGATTCTCC
4501  TGCTTCGGTC TCCCAATAGC TAAGACTACA GTAGTCCACC ACCATATCCA
4551  GATAATTTTT AAATTTTTG GGGGCCGGG CACAGTGGCT CACGCCTGTA
4601  ATCCCAACAC CATGGGAGGC TGAGATGGGT GGATCACGAG GTCAGGAGTT
```

Fig.1(Cont.)

```
4651  TGAGACCAGC CTGACCAACA TGGTGAAACT CTGTCTCTAC TAAAAAAAAA
4701  AAAAATAGAA AAATTAGCCG GGCGTGGTGG CACACGGCAC CTGTAATCCC
4751  AGCTACTGAG GAGGCTGAGG CAGGAGAATC ACTTGAACCC AGAAGGCAGA
4801  GGTTGCAATG AGCCGAGATT GCGCCACTGC ACTCCAGCCT GGGTGACAGA
4851  GTGAGACTCT GTCTCAAAAA AAAAAATTT TTTTTTTTT TTTGTAGAGA
4901  TGGATCTTGC TTTGTTTCTC TGGTTGGCCT TGAACTCCTG GCTTCAAGTG
4951  ATCCTCCTAC CTTGGCCTCG AAAGTGTTG GGATTACAGG CGTGAGCCAC
5001  CATGACTGAC CTGTCGTTAA TCTTGAGGTA CATAAACCTG GCTCCTAAAG
5051  GCTAAAGGCT AAATATTTGT TGGAGAAGGG GCATTGGATT TTGCATGAGG
5101  ATGATTCTGA CCTGGGAGGG CAGGTCAGCA GGCATCTCTG TTGCACAGAT
5151  AGAGTGTACA GGTCTGGAGA ACAAGGAGTG GGGGGTTATT GGAATTCCAC
5201  ATTGTTTGCT GCACGTTGGA TTTTGAAATG CTAGGGAACT TTGGGAGACT
5251  CATATTTCTG GGCTAGAGGA TCTGTGGACC ACAAGATCTT TTTATGATGA
5301  CAGTAGCAAT GTATCTGTGG AGCTGGATTC TGGGTTGGGA GTGCAAGGAA
5351  AAGAATGTAC TAAATGCCAA GACATCTATT TCAGGAGCAT GAGGAATAAA
5401  AGTTCTAGTT TCTGGTCTCA GAGTGGTGCA GGGATCAGGG AGTCTCACAA
5451  TCTCCTGAGT GCTGGTGTCT TAGGGCACAC TGGGTCTTGG AGTGCAAAGG
5501  ATCTAGGCAC GTGAGGCTTT GTATGAAGAA TCGGGGATCG TACCCACCCC
5551  CTGTTTCTGT TTCATCCTGG GCATGTCTCC TCTGCCTTTG TCCCTAGAT
5601  GAAGTCTCCA TGAGCTACAG GGCCTGGTGC ATCCAGGGTG ATCTAGTAAT
5651  TGCAGAACAG CAAGTGCTAG CTCTCCCTCC CCTTCCACAG CTCTGGGTGT
5701  GGGAGGGGGT TGTCCAGCCT CCAGCAGCAT GGGGAGGGCC TTGGTCAGCC
5751  TCTGGGTGCC AGCAGGGCAG GGCGGAGTC CTGGGGAATG AAGGTTTTAT
5801  AGGGCTCCTG GGGGAGGCTC CCCAGCCCCA AGCTTACCAC CTGCACCCGG
```

Fig.1(Cont.)

```
5851  AGAGCTGTGT CACCATGTGG GTCCCGGTTG TCTTCCTCAC CCTGTCCGTG
5901  ACGTGGATTG GTGAGAGGGG CCATGGTTGG GGGGATGCAG GAGAGGGAGC
5951  CAGCCCTGAC TGTCAAGCTG AGGCTCTTTC CCCCCAACC  CAGCACCCCA
6001  GCCCAGACAG GGAGCTGGGC TCTTTTCTGT CTCTCCCAGC CCCACTCCAA
6051  GCCCATACCC CCAGCCCCTC CATATTGCAA CAGTCCTCAC TCCCACACCA
6101  GGTCCCCGCT CCCTCCCACT TACCCCAGAA CTTTCTCCCC ATTTGCCCAG
6151  CCAGCTCCCT GCTCCCAGCT GCTTTACTAA AGGGGAAGTT CCTGGGCATC
6201  TCCGTGTTTC TCTTTGTGGG GCTCAAAACC TCCAAGGACC TCTCTCAATG
6251  CCATTGGTTC CTTGGACCGT ATCACTGGTC CACCTCCTGA GCCCCTCAAT
6301  CCTATCACAG TCTACTGACT TTTCCATTCA GCTGTGAGTG CCCAACCCTA
6351  TCCCAGAGAC CTTGATGCTT GGCCTCCCAA TCTTGCCCTA GGATACCCAG
6401  ATGCCAACCA GACACCTCCT TCTTCCTAGC CAGGCTATCT GGCTGAGACA
6451  ACAAATGGGT CCCTCAGTCT GGCAATGGGA CTCTGAGAAC TCCTCATTCC
6501  CTGACTCTTA GCCCCAGACT CTTCATTCAG TGGCCCACAT TTTCCTTAGG
6551  AAAAACATGA GCATCCCCAG CCACAACTGC CAGCTCTCTG ATTCCCCAAA
6601  TCTGCATCCT TTTCAAAACC TAAAAACAAA AAGAAAAACA AATAAAACAA
6651  AACCAACTCA GACCAGAACT GTTTTCTCAA CCTGGGACTT CCTAAACTTT
6701  CCAAAACCTT CCTCTTCCAG CAACTGAACC TCCCGATAAG GCACTTATCC
6751  CTGGTTCCTA GCACCGCTTA TCCCCTCAGA ATCCACAACT TGTACCAAGT
6801  TTCCTTCTC  CCAGTCCAAG ACCCAAATC  ACCACAAAGG ACCCAATCCC
6851  CAGACTCAAG ATATGGTCTG GGCTGTCTT  GTGTCTCCTA CCCTGATCCC
6901  TGGGTTCAAC TCTGTCCCAG AGCATGAAGC CTCTCCACCA GCACCAGCCA
6951  CCAACCTGCA AACCTAGGGA AGATTGACAG AATTCCCAGC CTTTCCCAGC
```

Fig.1(Cont.)

```
7001  TCCCCCTGCC CATGTCCCAG GACTCCCAGC CTTGGTTCTC TGCCCCCGTG
7051  TCTTTTCAAA CCCACATCCT AAATCCATCT CCTATCCGAG TCCCCCAGTT
7101  CCTCCTGTCA ACCCTGATTC CCCTGATCTA GCACCCCTC TGCAGGTGCT
7151  GCACCCCTCA TCCTGTCTCG GATTGTGGGA GGCTGGGAGT GCGAGAAGCA
7201  TTCCCAACCC TGGCAGGTGC TTGTGGCCTC TCGTGGCAGG GCAGTCTGCG
7251  GCGGTGTTCT GGTGCACCCC CAGTGGGTCC TCACAGCTGC CCACTGCATC
7301  AGGAAGTGAG TAGGGGCCTG GGTCTGGGG AGCAGGTGTC TGTGTCCAGA
7351  GGAATAACAG CTGGGCATTT TCCCCAGGAT AACCTCTAAG GCCAGCCTTG
7401  GGACTGGGGG AGAGAGGGAA AGTTCTGGTT CAGGTCACAT GGGGAGGCAG
7451  GGTTGGGGCT GGACCACCCT CCCCATGGCT GCCTGGGTCT CCATCTGTGT
7501  TCCTCTATGT CTCTTTGTGT CGCTTTCATT ATGTCTCTTG GTAACTGGCT
7551  TCGGTTGTGT CTCTCCGTGT GACTATTTTG TTCTCTCTCT CCCTCTCTTC
7601  TCTGTCTTCA GTCTCCATAT CTCCCCCTCT CTCTGTCCTT CTCTGGTCCC
7651  TCTCTAGCCA GTGTGTCTCA CCCTGTATCT CTCTGCCAGG CTCTGTCTCT
7701  CGGTCTCTGT CTCACCTGTG CCTTCTCCCT ACTGAGCACA CGCATGGGAT
7751  GGGCCTGGGG GGACCCTGAG AAAAGGAAGG GCTTTGGCTG GGCGCGGTGG
7801  CTCACACCTG TAATCCCAGC ACTTTGGGAG GCCAAGGCAG GTAGATCACC
7851  TGAGGTCAGG AGTTCGAGAC CAGCCTGGCC AACTGGTGAA ACCCCATCTC
7901  TACTAAAAAT ACAAAAAATT AGCCAGGCGT GGTCGGCGCA TGCCTGTAGT
7951  CCCAGCTACT CAGGAGGCTG AGGGAGGAGA ATTGCTTGAA CCTGGGAGGT
8001  GGAGGTTGCA GTGAGCCGAG ACGTGCCACT GCACTCCAGC CTGGGTGACA
8051  GAGTGAGACT CCGCCTCAAA AAAAAAAAA AAAAAAAGA AAGAAAAGA
8101  AAGAAAAGG AAGTGTTTTA TCCCTGATGT GTGTGGGTAT GAGGGTATGA
8151  GAGGGCCCCT CTCACTCCAT TCCTTCTCCA GGACATCCCT CCACTCTTGG
8201  GAGACACAGA GAAGGGCTGG TTCAGCTGGA GCTGGGAGGG GCAATTGAGG
```

Fig.1(Cont.)

```
8251  GAGGAGGAAG GAGAAGGGGG AAGGAAAACA GGGTATGGGG GAAAGGACCC

8301  TGGGGAGCGA AGTGGAGGAT ACAACCTTGG GCCTGCAGGC CAGGCTACCT

8351  ACCCACTTGG AAACCCACGC CAAAGCCGCA TCTACAGCTG AGCCACTCTG

8401  AGGCCTCCCC TCCCCAGCGG TCCCCACTCA GCTCCAAAGT CTCTCTCCCT

8451  TTTCTCTCCC ACACTCTATC ATCCCCCGGA TTCCTCTCTA CTTGGTTCTC

8501  ATTCTTCCTT TGACTTCCTG CTTCCCTTTC TCATTCATCT GTTTCTCACT

8551  TTCTGCCTGG TTTTGTTCTT CTCTCTCTCT TTCTCTGGCC CATGTCTGTT

8601  TCTCTATGTT TCTGTCTTTT CTTTCTCATC CTGTGTATTT TCGGCTCACC

8651  TTGTTTGTCA CTGTTCTCCC CTCTGCCCTT TCATTCTCTC TGTCCTTTTA

8701  CCCTCTTCCT TTTTCCCTTG GTTTCTCTCA GTTTCTGTAT CTGCCCTTCA

8751  CCCTCTCACA CTGCTGTTTC CCAACTCGTT GTCTGTATTT TTGGCCTGAA

8801  CATGTGTCTT CCCCAACCCT GTGTTTTTCT CACTGTTTCT TTTTCTCTTT

8851  TGGAGCCTCC TCCTTGCTCC TCTGTCCCTT CTCTCTTTCC TTATCATCCT

8901  CGCTCCTCAT TCCTGCGTCT GCTTCCTCCC CAGCAAAAGC GTGATCTTGC

8951  TGGGTCGGCA CAGCCTGTTT CATCCTGAAG ACACAGGCCA GGTATTTCAG

9001  GTCAGCCACA GCTTCCCACA CCCGCTCTAC GATATGAGCC TCCTGAAGAA

9051  TCGATTCCTC AGGCCAGGTG ATGACTCCAG CCACGACCTC ATGCTGCTCC

9101  GCCTGTCAGA GCCTGCCGAG CTCACGGATG CTGTGAAGGT CATGGACCTG

9151  CCCACCCAGG AGCCAGCACT GGGGACCACC TGCTACGCCT CAGGCTGGGG

9201  CAGCATTGAA CCAGAGGAGT GTACGCCTGG GCCAGATGGT GCAGCCGGGA

9251  GCCCAGATGC CTGGGTCTGA GGGAGGAGGG GACAGGACTC CTAGGTCTGA

9301  GGGAGGAGGG CCAAGGAACC AGGTGGGGTC CAGCCCACAA CAGTGTTTTT

9351  TGCCTGGCCC GTAGTCTTGA CCCCAAAGAA ACTTCAGTGT GTGGACCTCC
```

Fig.1(Cont.)

```
9401  ATGTTATTTC CAATGACGTG TGTGCGCAAG TTCACCCTCA GAAGGTGACC

9451  AAGTTCATGC TGTGTGCTGG ACGCTGGACA GGGGGCAAAA GCACCTGCTC

9501  GGTGAGTCAT CCCTACTCCC AAGATCTTGA GGGGAAAGGT GAGTGGGGAC

9551  CTTAATTCTG GCTGGGGTC TAGAAGCCAA CAAGCATCTG CCTCCCTGC

9601  TCCCCAGCTG TAGCCATGCC ACCTCCCCGT GTCTCATCTC ATTCCCTCCT

9651  TCCCTCTTCT TTGACTCCCT CAAGGCAATA GGTTATTCTT ACAGCACAAC

9701  TCATCTGTTC CTGCGTTCAG CACACGGTTA CTAGGCACCT GCTATGCACC

9751  CAGCACTGCC CTAGAGCCTG GACATAGCAG TGAACAGACA GAGAGCAGCC

9801  CCTCCCTTCT GTAGCCCCCA AGCCAGTGAG GGCACAGGC AGGAACAGGG

9851  ACCACAACAC AGAAAAGCTG GAGGGTGTCA GGAGGTGATC AGGCTCTCGG

9901  GGAGGGAGAA GGGGTGGGGA GTGTGACTGG GAGGAGACAT CCTGCAGAAG

9951  GCGGGAGTGA GCAAACACCT GCCGCAGGGG AGGGAGGGC CTGCGGCACC

10001 TGGGGGAGCA GAGGGAACAG CATCTGGCCA GGCCTGGGAG GAGGGGCCTA

10051 GAGGGCGTCA GGAGCAGAGA GGAGGTTGCC TGGCTGGAGT GAAGGATCGG

10101 GGCAGGGTGC GAGAGGGAAG AAGGACCCCT CCTGCAGGGC CTCACCTGGG

10151 CCACAGGAGG ACACTGCTTT TCCTCTGAGG AGTCAGGAAC TGTGGATGGT

10201 GCTGGACAGA AGCAGGACAG GGCCTGGCTC AGGTGTCCAG AGGCTGCCGC

10251 TGGCCTCCCT ATGGGATCAG ACTGCAGGGA GGGAGGGCAG CAGGGATGTG

10301 GAGGGAGTGA TGATGGGGCT GACCTGGGGG TGGCTCCAGG CATTGTCCCC

10351 ACCTGGGCCC TTACCCAGCC TCCCTCACAG GCTCCTGGCC CTCAGTCTCT

10401 CCCCTCCACT CCATTCTCCA CCTACCCACA GTGGGTCATT CTGATCACCG

10451 AACTGACCAT GCCAGCCCTG CCGATGGTCC TCCATGGCTC CCTAGTGCCC

10501 TGGAGAGGAG GTGTCTAGTC AGAGAGTAGT CCTGGAAGGT GGCCTCTGTG

10551 AGGAGCCACG GGACAGCAT CCTG
```

Fig.1(Cont.)

MWVPVVFLTLSVTWIGAAPLILSRIVGGWECEKHSQPWQVLVAS
RGRAVCGGVLVHPQWVLTAAHCIRKCKSVILLGRHSLFHPEDTGQVFQVSHSFPHPLY
DMSLLKNRFLRPGDDSSHDLMLLRLSEPAELTDAVKVMDLPTQEPALGTTCYASGWGS
IEPEEFLTPKKLQCVDLHVISNDVCAQVHPQKVTKFMLCAGRWTGGKSTCSGDSGGPL
VCNGVLQGITSWGSEPCALPERPSLYTKVVHYRKWIKDTIVANP

Fig. 2

```
           1
psal_1     MKNRGSYPPP VSVSSWACLL CLCPLDEVSM SYRAWCIQGD LVIAEQQVLA
psal_2     MKNRGSYPPP VSVSSWACLL CLCPLDEVSM SYRAWCIQGD LVIAEQQVLA
psal_0     ~~~~~~~~~~ ~~~~~~~~~~ ~~~~~~~~~~ ~~~~~~~~~~ ~~~~~~~~~~
humpsantig MKNRGSYPPP VSVSSWACLL CLCPLDEVSM SYRAWCIQGD LVIAEQQVLA
psal_5     MKNRGSYPPP VSVSSWACLL CLCPLDEVSM SYRAWCIQGD LVIAEQQVLA
psal_6     MKNRGSYPPP VSVSSWACLL CLCPLDEVSM SYRAWCIQGD LVIAEQQVLA 51                                                  100
psal_1     LPPLPQLWVW EGVVQPPAAW GGPWSASGCQ QGRGGVLGNE GFIGLLGEAP
psal_2     LPPLPQLWVW EGVVQPPAAW GGPWSASGCQ QGRGGVLGNE GFIGLLGEAP
psal_0     ~~~~~~~~~~ ~~~~~~~~~~ ~~~~~~~~~~ ~~~~~~~~~~ ~~~~~~~~~~
humpsantig LPPLPQLWVW EGVVQPPAAW GGPWSASGCQ QGRGGVLGNE GFIGLLGEAP
psal_5     LPPLPQLWVW EGVVQPPAAW GGPWSASGCQ QGRGGVLGNE GFIGLLGEAP
psal_6     LPPLPQLWVW EGVVQPPAAW GGPWSASGCQ QGRGGVLGNE GFIGLLGEAP 101                                                 150
psal_1     QPQAYHLHPE SCVTMWVPVV FLTLSVTWIG ERGHGWGDAG EGASPDCQAE
psal_2     QPQAYHLHPE SCVTMWVPVV FLTLSVTWIG ERGHGWGDAG EGASPDCQAE
psal_0     ~~~~~~~~~~ ~~~MWVPVV FLTLSVTWIG ERGHGWGDAG EGASPDCQAE
humpsantig QPQAYHLHPE SCVTMWVPVV FLTLSVTWIG ERGHGWGDAG EGASPDCQAE
psal_5     QPQAYHLHPE SCVTMWVPVV FLTLSVTWIG ERGHGWGDAG EGASPDCQAE
psal_6     QPQAYHLHPE SCVTMWVPVV FLTLSVTWIG ............
```

Fig. 3

```
              151                                                       200
psal_1        ALSPPTQHPS  PDRELGSFLS  LPAPLQ.....  .AHTPSPS  ILQQSSLPHQ
psal_2        ALSPPTQHPS  PDRELGSFLS  LPAPLQ.....  .AHTPSPS  ILQQSSLPHQ
psal_0        ALSPPTQHPS  PDRELGSFLS  LPAPLQ.....  .AHTPSPS  ILQQSSLPHQ
humpsantig    ALSPPTQHPS  PDRELGSFLS  LPAPLQ.....  .AHTPSPS  ILQQSSLPHQ
psal_5        ALSPPTQHPS  PDRELGSFLS  LPAPLQLPAP   SCL~~~~~  ~~~~~~~~~~
psal_6        ~~~~~~~~~~  ~~~~~~~~~~  ..........   ........  ..........

201                                                       250
psal_1        VPAPSHLPQN  FLPIAQPAPC  SQLLY~~~~~   ~~~~~~~~  ~~~~~~~~~~
psal_2        VPAPSHLPQN  FLPIAQPAPC  SQLLY~~~~~   ~~~~~~~~  ~~~~~~~~~~
psal_0        VPAPSHLPQN  FLPIAQPAPC  SQLLY~~~~~   ~~~~~~~~  ~~~~~~~~~~
humpsantig    VPAPSHLPQN  FLPI......  .....CPASS   LLPAALLKGK FLGISVFLFV
psal_5        ~~~~~~~~~~  ~~~~~~~~~~  ~~~~~~~~~~   ~~~~~~~~  ~~~~~~~~~~
psal_6        ..........  ..........  ..........   ........  ..........

251                                                       300
psal_1        ~~~~~~~~~~  ~~~~~~~~~~  ~~~~~~~~~~   ~~~~~~~~  ~~~~~~~~~~
psal_2        ~~~~~~~~~~  ~~~~~~~~~~  ~~~~~~~~~~   ~~~~~~~~  ~~~~~~~~~~
psal_0        ~~~~~~~~~~  ~~~~~~~~~~  ~~~~~~~~~~   ~~~~~~~~  ~~~~~~~~~~
humpsantig    GLKTSKDLSQ  CHWFLGPYHW  STS~~~~~~~   ...AAPLILS RIVGGWECEK HSQPWQVLVA
psal_5        ~~~~~~~~~~  ~~~~~~~~~~  ~~~~~~~~~~   ~~~~~~~~  ~~~~~~~~~~
psal_6        ~~~~~~~~~~  ~~~~~~~~~~  ~~~~~~~~~~   ~~~~~~~~  ~~~~~~~~~~
```

Fig. 3 (Cont.)

```
                     301                                                                        350
          psal_1     ??????????  ??????????  ??????????  ??????????  ??????????  ??????????
          psal_2     ??????????  ??????????  ??????????  ??????????  ??????????  ??????????
          psal_0     ??????????  ??????????  ??????????  ??????????  ??????????  ??????????
          humpsantig ??????????  ??????????  ??????????  ??????????  ??????????  ??????????
          psal_5     ??????????  ??????????  ??????????  ??????????  ??????????  ??????????
          psal_6     SRGRAVCGGV  LVHPQWVLTA  AHCIRNKSVI  LLGRHSLFHP  EDTGQVFQVS
                     351                                                                        400
          psal_1     ??????????  ??????????  ??????????  ??????????  ??????????  ??????????
          psal_2     ??????????  ??????????  ??????????  ??????????  ??????????  ??????????
          psal_0     ??????????  ??????????  ??????????  ??????????  ??????????  ??????????
          humpsantig ??????????  ??????????  ??????????  ??????????  ??????????  ??????????
          psal_5     ??????????  ??????????  ??????????  ??????????  ??????????  ??????????
          psal_6     HSFPHPLYDM  SLLKNRFLRP  GDDSSHDLML  LRLSEPAELT  DAVKVMDLPT
                     401                                                                        450
          psal_6     QEPALGTTCY  ASGWGSIEPE  EFLTPKKLQC  VDLHVISNDV  CAQVHPQKVT
                     451                                                                        500
          psal_6     KFMLCAGRWT  GGKSTCSGDS  GGPLVCNGVL  QGITSWGSEP  CALPERPSLY
                                 501         518
                     psal_6      TKVVHYRKWI  KDTIVANP
```

Fig. 3(Cont.)

```
             1
psal_1       MKNRGSYPPP  VSVSSWACLL  CLCPLDEVSM  SYRAWCIQGD  LVIAEQQVLA
psal_2       MKNRGSYPPP  VSVSSWACLL  CLCPLDEVSM  SYRAWCIQGD  LVIAEQQVLA
psal_0       ~~~~~~~~~~  ~~~~~~~~~~  ~~~~~~~~~~  ~~~~~~~~~~  ~~~~~~~~~~
humpsantig   MKNRGSYPPP  VSVSSWACLL  CLCPLDEVSM  SYRAWCIQGD  LVIAEQQVLA
psal_5       MKNRGSYPPP  VSVSSWACLL  CLCPLDEVSM  SYRAWCIQGD  LVIAEQQVLA
psal_6       MKNRGSYPPP  VSVSSWACLL  CLCPLDEVSM  SYRAWCIQGD  LVIAEQQVLA 51                                                     100
psal_1       LPPLPQLWVW  EGVVQPPAAW  GGPWSASGCQ  QGRGGVLGNE  GFIGLLGEAP
psal_2       LPPLPQLWVW  EGVVQPPAAW  GGPWSASGCQ  QGRGGVLGNE  GFIGLLGEAP
psal_0       ~~~~~~~~~~  ~~~~MWVPVV  ~~~~~~~~~~  ~~~~~~~~~~  ~~~~~~~~~~
humpsantig   LPPLPQLWVW  EGVVQPPAAW  GGPWSASGCQ  QGRGGVLGNE  GFIGLLGEAP
psal_5       LPPLPQLWVW  EGVVQPPAAW  GGPWSASGCQ  QGRGGVLGNE  GFIGLLGEAP
psal_6       LPPLPQLWVW  EGVVQPPAAW  GGPWSASGCQ  QGRGGVLGNE  GFIGLLGEAP 101                                                    150
psal_1       QPQAYHLHPE  SCVTMWVPVV  FLTLSVTWIG  ERGHGWGDAG  EGASPDCQAE
psal_2       QPQAYHLHPE  SCVTMWVPVV  FLTLSVTWIG  ERGHGWGDAG  EGASPDCQAE
psal_0       ~~~~~~~~~~  ~~~~MWVPVV  FLTLSVTWIG  ERGHGWGDAG  EGASPDCQAE
humpsantig   QPQAYHLHPE  SCVTMWVPVV  FLTLSVTWIG  ERGHGWGDAG  EGASPDCQAE
psal_5       QPQAYHLHPE  SCVTMWVPVV  FLTLSVTWIG  ERGHGWGDAG  EGASPDCQAE
psal_6       QPQAYHLHPE  SCVTMWVPVV  FLTLSVTWIG  .........
```

Fig. 4

```
           151
psal_1     ALSPPTQHPS PDRELGSFLS LPAPLQ..... ...AHTPSPS ILQQSSLPHQ  200
psal_2     ALSPPTQHPS PDRELGSFLS LPAPLQ..... ...AHTPSPS ILQQSSLPHQ
psal_0     ALSPPTQHPS PDRELGSFLS LPAPLQ..... ...AHTPSPS ILQQSSLPHQ
humpsantig ALSPPTQHPS PDRELGSFLS LPAPLQ..... ...AHTPSPS ILQQSSLPHQ
psal_5     ALSPPTQHPS PDRELGSFLS LPAPLQLPAP  SCL~~~~~~~ ~~~~~~~~~~
psal_6     ~~~~~~~~~~ ~~~~~~~~~~ .......... .......... ..........

201
psal_1     VPAPSHLPQN FLPIAQPAPC SQLLY~~~~~ ~~~~~~~~~~ ~~~~~~~~~~  250
psal_2     VPAPSHLPQN FLPIAQPAPC SQLLY~~~~~ ~~~~~~~~~~ ~~~~~~~~~~
psal_0     VPAPSHLPQN FLPIAQPAPC SQLLY~~~~~ ~~~~~~~~~~ ~~~~~~~~~~
humpsantig VPAPSHLPQN FLPI...... .....CPASS LLPAALLKGK FLGISVFLFV
psal_5     ~~~~~~~~~~ ~~~~~~~~~~ ~~~~~~~~~~ ~~~~~~~~~~ ~~~~~~~~~~
psal_6     .......... .......... .......... .......... ..........

251
psal_1     ~~~~~~~~~~ ~~~~~~~~~~ ~~~~~~~~~~ ~~~~~~~~~~ ~~~~~~~~~~  300
psal_2     ~~~~~~~~~~ ~~~~~~~~~~ ~~~~~~~~~~ ~~~~~~~~~~ ~~~~~~~~~~
psal_0     ~~~~~~~~~~ ~~~~~~~~~~ ~~~~~~~~~~ ~~~~~~~~~~ ~~~~~~~~~~
humpsantig GLKTSKDLSQ CHWFLGPYHW STS~~~~~~~ ~~~~~~~~~~ ~~~~~~~~~~
psal_5     ~~~~~~~~~~ ~~~~~~~~~~ ~~~~~~~~~~ ~~~~~~~~~~ ~~~~~~~~~~
psal_6     .......... .......... ...AAPLILS RIVGWECEK HSQPWQVLVA
```

Fig. 4 (Cont.)

```
301                                                                              350
psal_1   ~~~~~~~~~~ ~~~~~~~~~~ ~~~~~~~~~~ ~~~~~~~~~~ ~~~~~~~~~~
psal_2   ~~~~~~~~~~ ~~~~~~~~~~ ~~~~~~~~~~ ~~~~~~~~~~ ~~~~~~~~~~
psal_0   ~~~~~~~~~~ ~~~~~~~~~~ ~~~~~~~~~~ ~~~~~~~~~~ ~~~~~~~~~~
humpsantig ~~~~~~~~~~ ~~~~~~~~~~ ~~~~~~~~~~ ~~~~~~~~~~ ~~~~~~~~~~
psal_5   ~~~~~~~~~~ ~~~~~~~~~~ ~~~~~~~~~~ ~~~~~~~~~~ ~~~~~~~~~~
psal_6   SRGRAVCGGV LVHPQWVLTA AHCIRNKSVI LLGRHSLFHP EDTGQVFQVS 351                                                                     400
psal_1   ~~~~~~~~~~ ~~~~~~~~~~ ~~~~~~~~~~ ~~~~~~~~~~ ~~~~~~~~~~
psal_2   ~~~~~~~~~~ ~~~~~~~~~~ ~~~~~~~~~~ ~~~~~~~~~~ ~~~~~~~~~~
psal_0   ~~~~~~~~~~ ~~~~~~~~~~ ~~~~~~~~~~ ~~~~~~~~~~ ~~~~~~~~~~
humpsantig ~~~~~~~~~~ ~~~~~~~~~~ ~~~~~~~~~~ ~~~~~~~~~~ ~~~~~~~~~~
psal_5   ~~~~~~~~~~ ~~~~~~~~~~ ~~~~~~~~~~ ~~~~~~~~~~ ~~~~~~~~~~
psal_6   HSFPHPLYDM SLLKNRFLRP GDDSSHDLML LRLSEPAELT DAVKVMDLPT 401                                                                     450
psal_6   QEPALGTTCY ASGWGSIEPE EFLTPKKLQC VDLHVISNDV CAQVHPQKVT 451                                                                     500
psal_6   KFMLCAGRWT GGKSTCSGDS GGPLVCNGVL QGITSWGSEP CALPERPSLY 501        518
psal_6   TKVVHYRKWI KDTIVANP
```

Fig. 4 (Cont.)

```
1 MWDLVLSIALSVGCTGEI 18
  ||||||||||||||||| :
1 MWDLVLSIALSVGCTGAV 18
```

Fig. 5

Northern blot analysis:
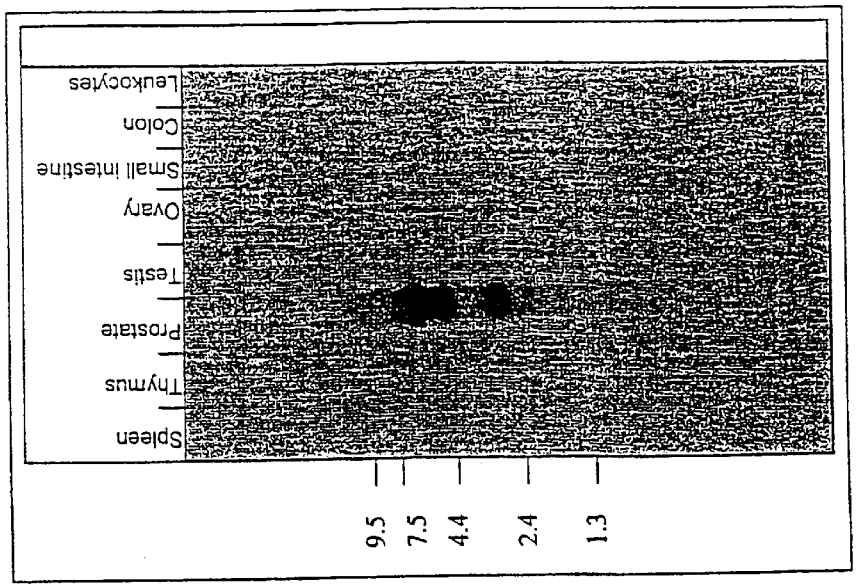
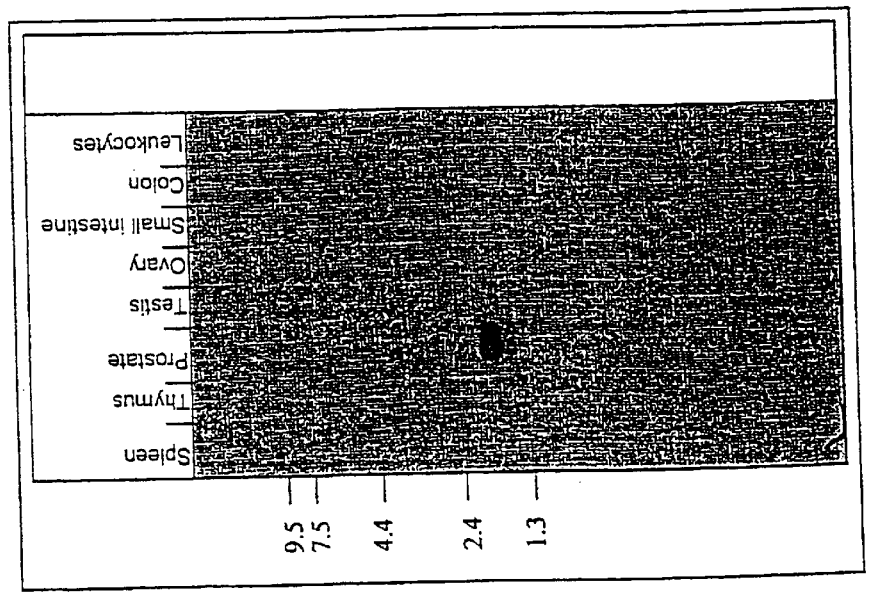
Fig. 7

Western blot analysis
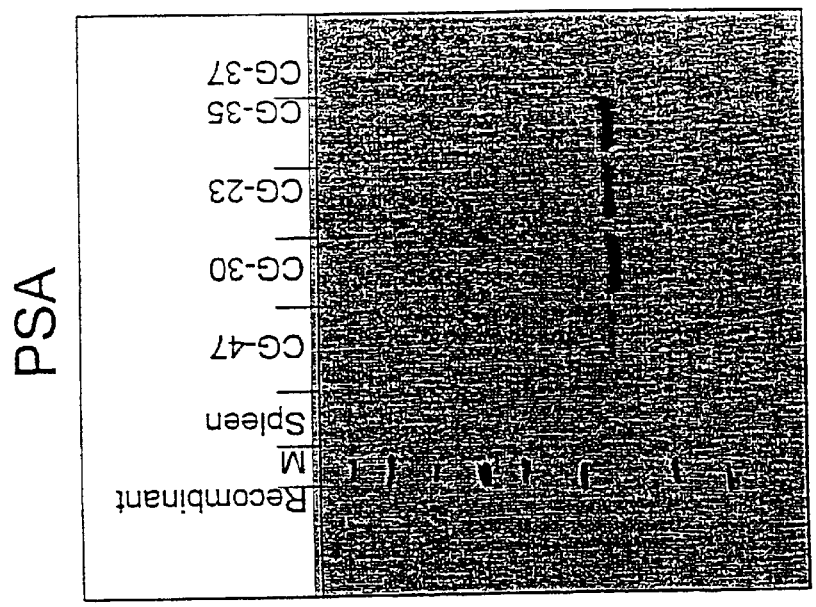
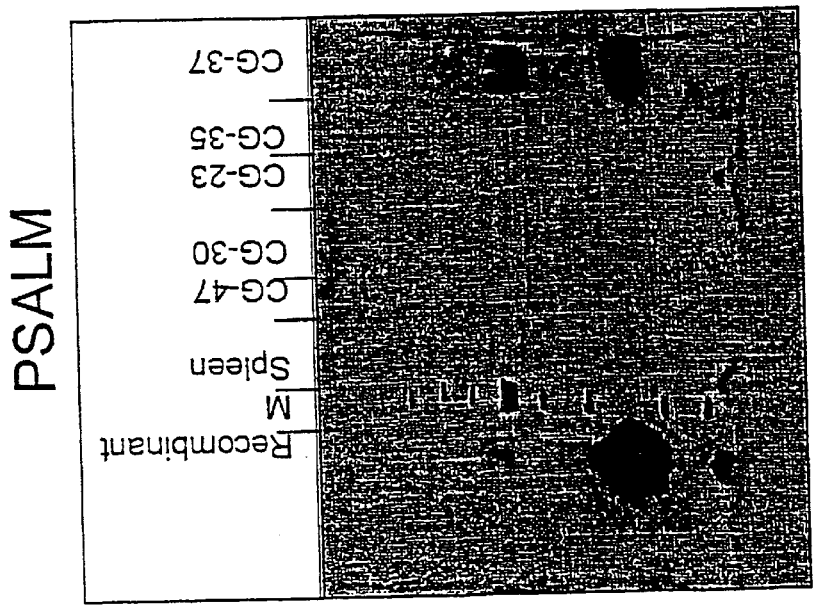
Fig. 8

PSALM
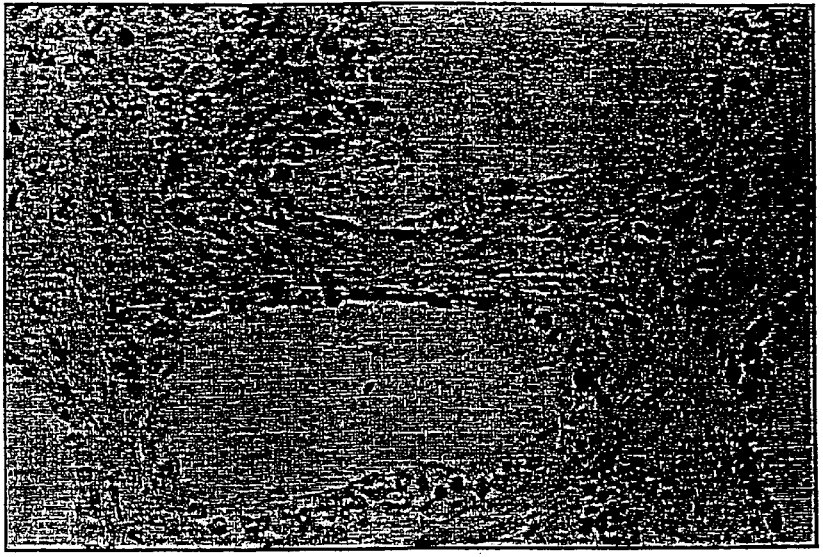
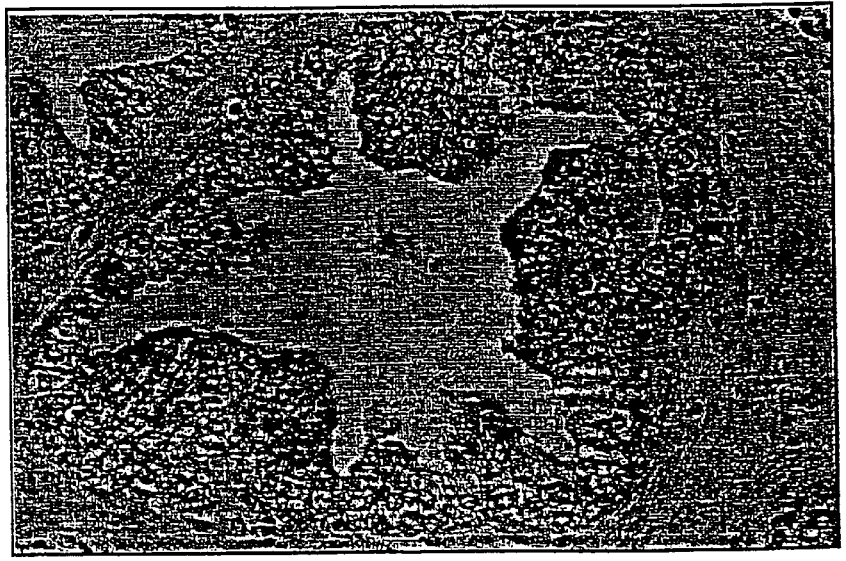
Fig. 9

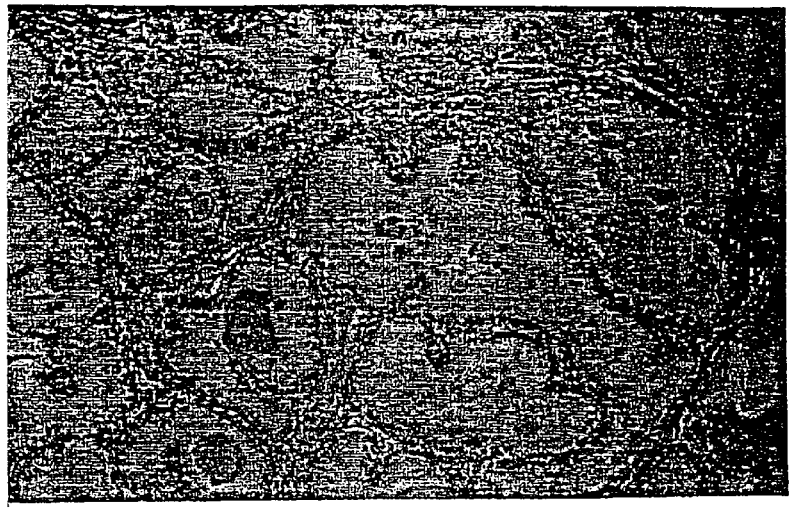
Fig. 10

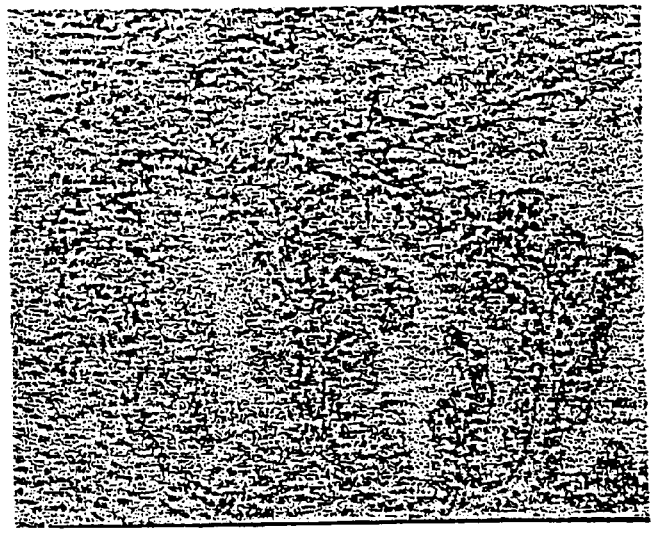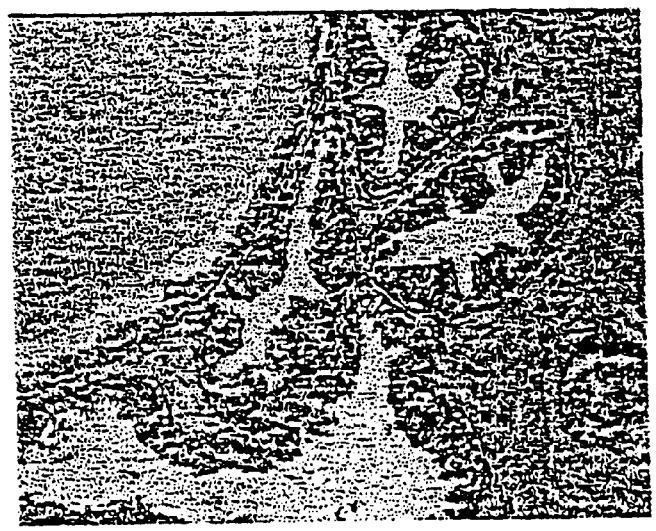
KLM
Fig. 12

SEQUENCE LISTING

<160> NUMBER OF SEQ ID NOS: 16

<210> SEQ ID NO 1
<211> LENGTH: 4661
<212> TYPE: DNA
<213> ORGANISM: Homo sapiens

<400> SEQUENCE: 1

```
attttgcatg ccaccttaat cttttttttt ttttttttaa atcgaggttt cagtctcatt      60
ctatttccca ggctggagtt caatagcgtg atcacagctc actgtagcct tgaactcctg     120
gccttaagag attctcctgc ttcggtctcc aatagctaa gactacagta gtccaccacc     180
atatccagat aattttaaa ttttttgggg ggccgggcac agtggctcac gcctgtaatc     240
ccaacaccat gggaggctga gatggtgga tcacgaggtc aggagtttga ccagcctg       300
accaacatgg tgaaactctg tctctactaa aaaaaaaaa aatagaaaaa ttagccgggc     360
gtggtggcac acggcacctg taatcccagc tactgaggag gctgaggcag gagaatcact     420
tgaacccaga aggcagaggt tgcaatgagc cgagattgcg ccactgcact ccagcctggg     480
tgacagagtg agactctgtc tcaaaaaaaa aaaattttt ttttttttt gtagagatgg       540
atcttgcttt gtttctctgg ttggccttga actcctggct tcaagtgatc ctcctacctt     600
ggcctcggaa agtgttggga ttacaggcgt gagccaccat gactgacctg tcgttaatct     660
tgaggtacat aaacctggct cctaaaggct aaaggctaaa tatttgttgg agaaggggca     720
ttggattttg catgaggatg attctgacct gggagggcag gtcagcaggc atctctgttg     780
cacagataga gtgtacaggt ctggagaaca aggagtgggg ggttattgga attccacatt     840
gtttgctgca cgttggattt tgaaatgcta gggaactttg ggagactcat atttctgggc     900
tagaggatct gtggaccaca agatctttt atgatgacga tagcaatgta tctgtgggagc     960
tggattctgg gttgggagtg caaggaaaag aatgtactaa atgccaagac atctatttca    1020
ggagcatgag gaataaaagt tctagtttct ggtctcagag tggtgcaggg atcagggagt    1080
ctcacaatct cctgagtgct ggtgtcttag gcacactgg gtcttggagt gcaaaggatc     1140
taggcacgtg aggctttgta tgaagaatcg gggatcgtac ccaccccctg tttctgtttc    1200
atcctgggcg tgtctcctct gcctttgtcc cctagatgaa gtctccatga gctacagggc    1260
ctggtgcatc cagggtgatc tagtaattgc agaacagcaa gtactagctc tccctcccct    1320
tccacagctc tgggtgtggg aggggttgt ccagcctcca gcagcatggg gagggccttg      1380
gtcagcctct gggtgccagc agggcagggg cggagtcctg gggaatgaag gttttatagg    1440
gctcctgggg gaggctcccc agccccaagc ttaccacctg cacccggaga gctgtgtcac    1500
catgtgggtc ccggttgtct tcctcaccct gtccgtgacg tggattggtg agaggggcca    1560
tggttggggg gatgcaggag agggagccag ccctgactgt caagctgagg ctctttcccc    1620
cccaacccag caccccagcc cagacaggga gctgggctct tttctgtctc tcccagcccc    1680
actccaagcc catacccca gccctccat attgcaacag tcctcactcc cacaccaggt      1740
ccccgctccc tcccacttac cccagaactt tctccccatt gccagccag ctccctgctc     1800
ccagctgctt tactaaaggg gaagttcctg ggcatctccg tgtttctctt tgtgggctc     1860
aaaacctcca aggacctctc tcaatgccat tggttccttg gaccgtatca ctggtccacc    1920
tcctgaggcc ctcaatccta tcacagtcta ctgactttc ccattcagct gtgagtgccc     1980
aaccctatcc cagagacctt gatgcttggc ctcccaatct tgccctagga tacccagatg    2040
```

```
ccaaccagac acctccttct tcctagccag gctatctggc ctgagacaac aaatgggtcc   2100
ctcagtctgg caatgggact ctgagaactc ctcattccct gactcttagc cccagactct   2160
tcattcagtg gcccacattt tccttaggaa aaacatgagc atccccagcc acaactgcca   2220
gctctctgat tccccaaatc tgcatccttt tcaaaaccta aaaacaaaaa gaaaaacaaa   2280
taaaacaaaa ccaactcaga ccagaactgt tttctcaacc tgggacttcc taaactttcc   2340
aaaaccttcc tcttccagca actgaacctc gccataaggc acttatccct ggttcctagc   2400
accccttatc ccctcagaat ccacaacttg taccaagttt cccttctccc agtccaagac   2460
cccaaatcac cacaaaggac ccaatcccca gactcaagat atggtctggg cgctgtcttg   2520
tgtctcctac cctgatccct gggttcaact ctgctcccag agcatgaagc ctctccacca   2580
gcaccagcca ccaacctgca aacctaggga agattgacag aattcccagc ctttccagc    2640 tcccctgcc catgtcccag gactcccagc cttggttctc tgccccgtg tcttttcaaa     2700 cccacatcct aaatccatct cctatccgag tcccccagtt cctcctgtca accctgattc   2760
ccctgatcta gcacccctc tgcaggtgct gcacccctca tcctgtctcg gattgtggga    2820
ggctgggagt gcgagaagca ttcccaaccc tggcaggtgc ttgtggcctc tcgtggcagg   2880
gcagtctgcg gcggtgttct ggtgcacccc cagtgggtcc tcacagctgc ccactgcatc   2940
aggaacaaaa gcgtgatctt gctgggtcgg cacagcctgt ttcatcctga agacacaggc   3000
caggtatttc aggtcagcca cagcttccca cacccgctct acgatatgag cctcctgaag   3060
aatcgattcc tcaggccagg tgatgactcc agccacgacc tcatgctgct ccgcctgtca   3120
gagcctgccg agctcacgga tgctgtgaag gtcatggacc tgcccaccca ggagccagca   3180
ctggggacca cctgctacgc ctcaggctgg ggcagcattg aaccagagga gttcttgacc   3240
ccaaagaaac ttcagtgtgt ggacctccat gttatttcca atgacgtgtg tgcgcaagtt   3300
caccctcaga aggtgaccaa gttcatgctg tgtgctggac gctggacagg gggcaaaagc   3360
acctgctcgg gtgattctgg gggcccactt gtctgtaatg gtgtgcttca aggtatcacg   3420
tcatggggca gtgaaccatg tgccctgccc gaaaggcctt ccctgtacac caaggtggtg   3480
cattaccgga agtggatcaa ggacaccatc gtggccaacc cctgagcacc cctatcaact   3540
ccctattgta gtaaacttgg aaccttggaa atgaccaggc caagactcaa gcctccccag   3600
ttctactgac ctttgtcctt aggtgtgagg tccagggttg ctaggaaaag aaatcagcag   3660
acacaggtgt agaccagagt gtttcttaaa tggtgtaatt ttgtcctctc tgtgtcctgg   3720
ggaatactgg ccatgcctgg agacatatca ctcaatttct ctgaggacac agataggatg   3780
gggtgtctgt gttatttgtg ggrtacagag atgaaagagg ggtgggwwcc acactgagag   3840
agtggagagt gacatgtgct ggacactgtc catgaagcac tgagcagaag ctggaggcac   3900
aacgcaccag acactcacag caaggatgga gctgaaaaca taacccactc tgtcctggag   3960
gcactgggaa gcctagagaa ggctgtgagc caaggaggga gggtcttcct ttggcatggg   4020
atggggatga agtaaggaga gggactggac cccctggaag ctgattcact atgggggag    4080 gtgtattgaa gtcctccaga caaccctcag atttgatgat tcctagtag  aactcacaga   4140 aataaagagc tsttatacgt ggtttattct ggtttgttac attgacagga gacacactga   4200
aatcagcaaa ggaaacaggc atctaagtgg ggatgtgaag aaaacaggga aaatctttca   4260
gttgttttct cccagtgggg tgttgtggac agcacttaaa tcacacagaa gtgatgtgtg   4320
accttgtgta tgaagtattt ccaactaagg aagctcacct gagccttagt gtccagagtt   4380
```

-continued

| | | | |
|---|---|---|---|
| cttattgggg | gtctgtagga | taggcatggg gtactggaat agctgacctt aacttctcag | 4440 |
| acctgaggtt | cccaagagtt | caagcagata cagcatggcc tagagcctca gatgtacaaa | 4500 |
| aacaggcatt | catcatgaat | cgcactgtta gcatgaatca tctggcacgg cccaaggccc | 4560 |
| caggtatacc | aaggcacttg | ggccgaatgt tccaagggat taaatgtcat ctcccaggag | 4620 |
| ttattcaagg | gtgagccctg | tacttggaac gttcaggctt t | 4661 |

<210> SEQ ID NO 2
<211> LENGTH: 4661
<212> TYPE: DNA
<213> ORGANISM: Homo sapiens

<400> SEQUENCE: 2

| | | | |
|---|---|---|---|
| attttgcatg | ccaccttaat | ctttttttt tttttttaa atcgaggttt cagtctcatt | 60 |
| ctatttccca | ggctggagtt | caatagcgtg atcacagctc actgtagcct tgaactcctg | 120 |
| gccttaagag | attctcctgc | ttcggtctcc caatagctaa gactacagta gtccaccacc | 180 |
| atatccagat | aattttttaaa | ttttttgggg ggccgggcac agtggctcac gcctgtaatc | 240 |
| ccaacaccat | gggaggctga | gatgggtgga tcacgaggtc aggagtttga gaccagcctg | 300 |
| accaacatgg | tgaaactctg | tctctactaa aaaaaaaaa aatagaaaaa ttagccgggc | 360 |
| gtggtggcac | acggcacctg | taatcccagc tactgaggag gctgaggcag gagaatcact | 420 |
| tgaacccaga | aggcagaggt | tgcaatgagc cgagattgcg ccactgcact ccagcctggg | 480 |
| tgacagagtg | agactctgtc | tcaaaaaaaa aaaattttttt ttttttttt gtagagatgg | 540 |
| atcttgcttt | gtttctctgg | ttggccttga actcctggct tcaagtgatc ctcctacctt | 600 |
| ggcctcggaa | agtgttggga | ttacaggcgt gagccaccat gactgacctg tcgttaatct | 660 |
| tgaggtacat | aaacctggct | cctaaaggct aaaggctaaa tatttgttgg agaaggggca | 720 |
| ttggattttg | catgaggatg | attctgacct gggagggcag gtcagcaggc atctctgttg | 780 |
| cacagataga | gtgtacaggt | ctggagaaca aggagtgggg ggttattgga attccacatt | 840 |
| gtttgctgca | cgttggattt | tgaaatgcta gggaactttg ggagactcat atttctgggc | 900 |
| tagaggatct | gtggaccaca | agatcttttt atgatgacag tagcaatgta tctgtggagc | 960 |
| tggattctgg | gttgggagtg | caaggaaaag aatgtactaa atgccaagac atctatttca | 1020 |
| ggagcatgag | gaataaaagt | tctagtttct ggtctcagag tggtgcaggg atcagggagt | 1080 |
| ctcacaatct | cctgagtgct | ggtgtcttag ggcacactgg gtcttggagt gcaaaggatc | 1140 |
| taggcacgtg | aggctttgta | tgaagaatcg gggatcgtac ccacccctg tttctgtttc | 1200 |
| atcctgggcg | tgtctcctct | gcctttgtcc cctagatgaa gtctccatga gctacagggc | 1260 |
| ctggtgcatc | cagggtgatc | tagtaattgc agaacagcaa gtactagctc tccctcccct | 1320 |
| tccacagctc | tgggtgtggg | aggggttgt ccagcctcca gcagcatggg gagggccttg | 1380 |
| gtcagcctct | gggtgccagc | agggcagggg cggagtcctg gggaatgaag gttttatagg | 1440 |
| gctcctgggg | gaggctcccc | agccccaagc ttaccacctg cacccggaga gctgtgtcac | 1500 |
| catgtgggtc | ccggttgtct | tcctcaccct gtccgtgacg tggattggtg agagggcca | 1560 |
| tggttggggg | gatgcaggag | agggagccag ccctgactgt caagctgagg ctctttcccc | 1620 |
| cccaacccag | caccccagcc | cagacaggga gctgggctct tttctgtctc tcccagcccc | 1680 |
| actccaagcc | catacccca | gcccctccat attgcaacag tcctcactcc cacaccaggt | 1740 |
| ccccgctccc | tcccacttac | cccagaactt tctccccatt gcccagccag ctccctgctc | 1800 |
| ccagctgctt | tactaaaggg | gaagttcctg ggcatctccg tgtttctctt tgtggggctc | 1860 |

-continued

```
aaaacctcca aggacctctc tcaatgccat tggttccttg gaccgtatca ctggtccacc   1920
tcctgaggcc ctcaatccta tcacagtcta ctgactttc ccattcagct gtgagtgccc    1980
aaccctatcc cagagacctt gatgcttggc ctcccaatct tgccctagga tacccagatg   2040
ccaaccagac acctccttct tcctagccag gctatctggc ctgagacaac aaatgggtcc   2100
ctcagtctgg caatgggact ctgagaactc ctcattccct gactcttagc cccagactct   2160
tcattcagtg gcccacattt tccttaggaa aaacatgagc atccccagcc acaactgcca   2220
gctctctgat tccccaaatc tgcatccttt tcaaaaccta aaaacaaaaa gaaaacaaa    2280 taaaacaaaa ccaactcaga ccagaactgt tttctcaacc tgggacttcc taaactttcc   2340
aaaaccttcc tcttccagca actgaacctc gccataaggc acttatccct ggttcctagc   2400
accccttatc ccctcagaat ccacaacttg taccaagttt ccttctccc agtccaagac    2460 cccaaatcac cacaaaggac ccaatcccca gactcaagat atggtctggg cgctgtcttg   2520
tgtctcctac cctgatccct gggttcaact ctgctcccag agcatgaagc ctctccacca   2580
gcaccagcca ccaacctgca aacctaggga agattgacag aattcccagc ctttcccagc   2640 tcccctgcc catgtcccag gactcccagc cttggttctc tgccccgtg tcttttcaaa     2700 cccacatcct aaatccatct cctatccgag tcccccagtt cctcctgtca accctgattc   2760
ccctgatcta gcaccccctc tgcaggtgct gcaccctca tcctgtctcg gattgtggga    2820
ggctgggagt gcgagaagca ttcccaaccc tggcaggtgc ttgtggcctc tcgtggcagg   2880
gcagtctgcg gcggtgttct ggtgcacccc cagtgggtcc tcacagctgc ccactgcatc   2940
aggaacaaaa gcgtgatctt gctgggtcgg cacagcctgt ttcatcctga agacacaggc   3000
caggtatttc aggtcagcca cagcttccca caccccgctct acgatatgag cctcctgaag   3060
aatcgattcc tcaggccagg tgatgactcc agccacgacc tcatgctgct ccgcctgtca   3120
gagcctgccg agctcacgga tgctgtgaag gtcatggacc tgcccaccca ggagccagca   3180
ctggggacca cctgctacgc ctcaggctgg ggcagcattg aaccagagga gttcttgacc   3240
ccaaagaaac ttcagtgtgt ggacctccat gttatttcca atgacgtgtg tgcgcaagtt   3300
caccctcaga aggtgaccaa gttcatgctg tgtgctggac gctggacagg gggcaaaagc   3360
acctgctcgg gtgattctgg gggcccactt gtctgtaatg gtgtgcttca aggtatcacg   3420
tcatggggca gtgaaccatg tgccctgccc gaaaggcctt ccctgtacac caaggtggtg   3480
cattaccgga agtggatcaa ggacaccatc gtggccaacc cctgagcacc cctatcaact   3540
ccctattgta gtaaacttgg aaccttggaa atgaccaggc caagactcaa gcctccccag   3600
ttctactgac ctttgtcctt aggtgtgagg tccagggttg ctaggaaaag aaatcagcag   3660
acacaggtgt agaccagagt gtttcttaaa tggtgtaatt ttgtcctctc tgtgtcctgg   3720
ggaatactgg ccatgcctgg agacatatca ctcaatttct ctgaggacac agataggatg   3780
gggtgtctgt gttatttgtg ggrtacagag atgaagagg ggtgggwwcc acactgagag    3840
agtggagagt gacatgtgct ggacactgtc catgaagcac tgagcagaag ctggaggcac   3900
aacgcaccag acactcacag caaggatgga gctgaaaaca taacccactc tgtcctggag   3960
gcactgggaa gcctagagaa ggctgtgagc caaggaggga gggtcttcct ttggcatggg   4020 atgggatga agtaaggaga gggactggac cccctggaag ctgattcact atgggggag    4080 gtgtattgaa gtcctccaga caaccctcag atttgatgat ttcctagtag aactcacaga   4140
aataaagagc tsttatacgt ggtttattct ggtttgttac attgacagga gacacactga   4200
```

-continued

| aatcagcaaa ggaaacaggc atctaagtgg ggatgtgaag aaaacaggga aaatctttca | 4260 |
| gttgttttct cccagtgggg tgttgtggac agcacttaaa tcacacagaa gtgatgtgtg | 4320 |
| accttgtgta tgaagtattt ccaactaagg aagctcacct gagccttagt gtccagagtt | 4380 |
| cttattgggg gtctgtagga taggcatggg gtactggaat agctgacctt aacttctcag | 4440 |
| acctgaggtt cccaagagtt caagcagata cagcatggcc tagagcctca gatgtacaaa | 4500 |
| aacaggcatt catcatgaat cgcactgtta gcatgaatca tctggcacgg cccaaggccc | 4560 |
| caggtatacc aaggcacttg ggccgaatgt tccaagggat taaatgtcat ctcccaggag | 4620 |
| ttattcaagg gtgagccctg tacttggaac gttcaggctt t | 4661 |

<210> SEQ ID NO 3
<211> LENGTH: 3846
<212> TYPE: DNA
<213> ORGANISM: Homo sapiens

<400> SEQUENCE: 3

| attttgcatg ccaccttaat cttttttttt tttttttttaa atcgaggttt cagtctcatt | 60 |
| ctatttccca ggctggagtt caatagcgtg atcacagctc actgtagcct tgaactcctg | 120 |
| gccttaagag attctcctgc ttcggtctcc caatagctaa gactacagta gtccaccacc | 180 |
| atatccagat aattttttaaa ttttttgggg ggccgggcac agtggctcac gcctgtaatc | 240 |
| ccaacaccat gggaggctga gatggtggat tcacgaggtc aggagtttga gaccagcctg | 300 |
| accaacatgg tgaaactctg tctctactaa aaaaaaaaaa aatagaaaaa ttagccgggc | 360 |
| gtggtggcac acggcacctg taatcccagc tactgaggag gctgaggcag gagaatcact | 420 |
| tgaacccaga aggcagaggt tgcaatgagc cgagattgcg ccactgcact ccagcctggg | 480 |
| tgacagagtg agactctgtc tcaaaaaaaa aaaattttttt ttttttttttt gtagagatgg | 540 |
| atcttgcttt gtttctctgg ttggccttga actcctggct tcaagtgatc ctcctacctt | 600 |
| ggcctcggaa agtgttggga ttacaggcgt gagccaccat gactgacctg tcgttaatct | 660 |
| tgaggtacat aaacctggct cctaaaggct aaaggctaaa tatttgttgg agaaggggca | 720 |
| ttggattttg catgaggatg attctgacct gggagggcag gtcagcaggc atctctgttg | 780 |
| cacagataga gtgtacaggt ctggagaaca aggagtgggg ggttattgga attccacatt | 840 |
| gtttgctgca cgttggattt tgaaatgcta gggaactttg ggagactcat atttctgggc | 900 |
| tagaggatct gtggaccaca agatcttttt atgatgacag tagcaatgta tctgtgggagc | 960 |
| tggattctgg gttgggagtg caaggaaaag aatgtactaa atgccaagac atctatttca | 1020 |
| ggagcatgag gaataaaagt tctagtttct ggtctcagag tggtgcaggg atcagggagt | 1080 |
| ctcacaatct cctgagtgct ggtgtcttag ggcacactgg gtcttggagt gcaaaggatc | 1140 |
| taggcacgtg aggctttgta tgaagaatcg ggatcgtac ccaccccctg tttcgtttc | 1200 |
| atcctgggcg tgtctcctct gcctttgtcc cctagatgaa gtctccatga gctacagggc | 1260 |
| ctggtgcatc caggtgatc tagtaattgc agaacagcaa gtactagctc tccctccct | 1320 |
| tccacagctc tgggtgtggg aggggttgt ccagcctcca gcagcatggg gagggccttg | 1380 |
| gtcagcctct gggtgccagc agggcagggg cggagtcctg gggaatgaag gttttatagg | 1440 |
| gctcctgggg gaggctcccc agccccaagc ttaccacctg cacccggaga gctgtgtcac | 1500 |
| catgtgggtc ccggttgtct tcctcaccct gtccgtgacg tggattggtg agagggggcca | 1560 |
| tggttggggg gatgcaggag agggagccag ccctgactgt caagctgagg ctctttcccc | 1620 |
| cccaacccag caccccagcc cagacaggga gctgggctct tttctgtctc tcccagcccc | 1680 |

```
actccaagcc cataccccca gcccctccat attgcaacag tcctcactcc cacaccaggt    1740
ccccgctccc tcccacttac cccagaactt tctccccatt gcccagccag ctccctgctc    1800
ccagctgctt tactaaaggg gaagttcctg ggcatctccg tgtttctctt tgtgggggctc   1860 aaaacctcca aggacctctc tcaatgccat tggttccttg daccgtatca ctggtccacc    1920
tcctgaggcc ctcaatccta tcacagtcta ctgactttc ccattcagct gtgctgcacc    1980
cctcatcctg tctcggattg tgggaggctg ggagtgcgag aagcattccc aaccctggca    2040
ggtgcttgtg gcctctcgtg gcagggcagt ctgcggcggt gttctggtgc accccagtg     2100 ggtcctcaca gctgcccact gcatcaggaa caaaagcgtg atcttgctgg gtcggcacag    2160
cctgtttcat cctgaagaca caggccaggt atttcaggtc agccacagct tcccacaccc    2220
gctctacgat atgagcctcc tgaagaatcg attcctcagg ccaggtgatg actccagcca    2280
cgacctcatg ctgctccgcc tgtcagagcc tgccgagctc acggatgctg tgaaggtcat    2340
ggacctgccc acccaggagc cagcactggg gaccacctgc tacgcctcag gctggggcag    2400
cattgaacca gaggagttct tgaccccaaa gaaacttcag tgtgtggacc tccatgttat    2460
ttccaatgac gtgtgtgcgc aagttcaccc tcagaaggtg accaagttca tgctgtgtgc    2520
tggacgctgg acagggggca aaagcacctg ctcgggtgat tctgggggcc cacttgtctg    2580
taatggtgtg cttcaaggta tcacgtcatg gggcagtgaa ccatgtgccc tgcccgaaag    2640
gccttccctg tacaccaagg tggtgcatta ccggaagtgg atcaaggaca ccatcgtggc    2700 caaccctga gcacccctat caactcccta ttgtagtaaa cttggaacct tggaaatgac    2760
caggccaaga ctcaagcctc cccagttcta ctgacctttg tccttaggtg tgaggtccag    2820
ggttgctagg aaaagaaatc agcagacaca ggtgtagacc agagtgtttc ttaaatggtg    2880
taattttgtc ctctctgtgt cctggggaat actggccatg cctggagaca tatcactcaa    2940
tttctctgag gacacagata ggatggggtg tctgtgttat ttgtgggrta cagagatgaa    3000 agagggtgg gwwccacact gagagagtgg agagtgacat gtgctggaca ctgtccatga    3060
agcactgagc agaagctgga ggcacaacgc accagacact cacagcaagg atggagctga    3120
aaacataacc cactctgtcc tggaggcact gggaagccta gagaaggctg tgagccaagg    3180
agggagggtc ttcctttggc atgggatggg gatgaagtaa ggagagggac tggaccccct    3240
ggaagctgat tcactatggg gggaggtgta ttgaagtcct ccagacaacc ctcagatttg    3300
atgatttcct agtagaactc acagaaataa agagctstta tacgtggttt attctggttt    3360
gttacattga caggagacac actgaaatca gcaaaggaaa caggcatcta agtggggatg    3420
tgaagaaaac agggaaaatc tttcagttgt tttctcccag tggggtgttg tggacagcac    3480
ttaaatcaca cagaagtgat gtgtgacctt gtgtatgaag tatttccaac taaggaagct    3540
cacctgagcc ttagtgtcca gagttcttat tgggggtctg taggataggc atggggtact    3600
ggaatagctg accttaactt ctcagacctg aggttcccaa gagttcaagc agatacagca    3660
tggcctagag cctcagatgt acaaaaacag gcattcatca tgaatcgcac tgttagcatg    3720
aatcatctgg cacggcccaa ggccccaggt ataccaaggc acttgggccg aatgttccaa    3780
gggattaaat gtcatctccc aggagttatt caagggtgag ccctgtactt ggaacgttca    3840
ggcttt                                                              3846
```

<210> SEQ ID NO 4
<211> LENGTH: 1709
<212> TYPE: DNA

<213> ORGANISM: Homo sapiens

<400> SEQUENCE: 4

```
attttgcatg ccaccttaat ctttttttt ttttttttaa atcgaggttt cagtctcatt      60
ctatttccca ggctggagtt caatagcgtg atcacagctc actgtagcct tgaactcctg    120
gccttaagag attctcctgc ttcggtctcc aatagctaa gactacagta gtccaccacc     180
atatccagat aattttttaaa ttttttgggg ggccgggcac agtggctcac gcctgtaatc   240
ccaacaccat gggaggctga gatgggtgga tcacgaggtc aggagtttga gaccagcctg    300
accaacatgg tgaaactctg tctctactaa aaaaaaaaa aatagaaaaa ttagccgggc     360
gtggtggcac acggcacctg taatcccagc tactgaggag gctgaggcag gagaatcact    420
tgaacccaga aggcagaggt tgcaatgagc cgagattgcg ccactgcact ccagcctggg    480
tgacagagtg agactctgtc tcaaaaaaaa aaattttttt tttttttttt gtagagatgg    540
atcttgcttt gtttctctgg ttggccttga actcctggct tcaagtgatc ctcctacctt    600
ggcctcggaa agtgttggga ttacaggcgt gagccaccat gactgacctg tcgttaatct    660
tgaggtacat aaacctggct cctaaaggct aaaggctaaa tatttgttgg agaaggggca    720
ttggattttg catgaggatg attctgacct gggagggcag gtcagcaggc atctctgttg    780
cacagataga gtgtacaggt ctggagaaca aggagtgggg ggttattgga attccacatt    840
gtttgctgca cgttggattt tgaaatgcta gggaactttg ggagactcat atttctgggc    900
tagaggatct gtggaccaca agatctttt atgatgacag tagcaatgta tctgtggagc    960
tggattctgg gttgggagtg caaggaaaag aatgtactaa atgccaagac atctatttca   1020
ggagcatgag gaataaaagt tctagtttct ggtctcagag tggtgcaggg atcagggagt   1080
ctcacaatct cctgagtgct ggtgtcttag ggcacactgg gtcttggagt gcaaaggatc   1140
taggcacgtg aggctttgta tgaagaatcg gggatcgtac ccaccccctg tttctgtttc   1200
atcctgggcg tgtctcctct gcctttgtcc cctagatgaa gtctccatga gctacagggc   1260
ctggtgcatc cagggtgatc tagtaattgc agaacagcaa gtactagctc tccctccccct   1320
tccacagctc tgggtgtggg aggggttgt ccagcctcca gcagcatggg gagggccttg    1380
gtcagcctct gggtgccagc agggcagggg cggagtcctg gggaatgaag gttttatagg   1440
gctcctgggg gaggctcccc agccccaagc ttaccacctg cacccggaga gctgtgtcac   1500
catgtgggtc ccggttgtct tcctcaccct gtccgtgacg tggattggtg agaggggcca   1560
tggttggggg gatgcaggag agggagccag ccctgactgt caagctgagg ctctttcccc    1620
cccaacccag caccccagcc cagacaggga gctgggctct tttctgtctc tcccagcccc   1680
actccaactc cctgctccca gctgcttaa                                      1709
```

<210> SEQ ID NO 5
<211> LENGTH: 3423
<212> TYPE: DNA
<213> ORGANISM: Homo sapiens

<400> SEQUENCE: 5

```
attttgcatg ccaccttaat ctttttttt ttttttttaa atcgaggttt cagtctcatt      60
ctatttccca ggctggagtt caatagcgtg atcacagctc actgtagcct tgaactcctg    120
gccttaagag attctcctgc ttcggtctcc aatagctaa gactacagta gtccaccacc     180
atatccagat aattttttaaa ttttttgggg ggccgggcac agtggctcac gcctgtaatc   240
ccaacaccat gggaggctga gatgggtgga tcacgaggtc aggagtttga gaccagcctg    300
```

-continued

```
accaacatgg tgaaactctg tctctactaa aaaaaaaaaa aatagaaaaa ttagccgggc    360
gtggtggcac acggcacctg taatcccagc tactgaggag gctgaggcag gagaatcact    420
tgaacccaga aggcagaggt tgcaatgagc cgagattgcg ccactgcact ccagcctggg    480
tgacagagtg agactctgtc tcaaaaaaaa aaaatttttt tttttttttt gtagagatgg    540
atcttgcttt gtttctctgg ttggccttga actcctggct tcaagtgatc ctcctacctt    600
ggcctcggaa agtgttggga ttacaggcgt gagccaccat gactgacctg tcgttaatct    660
tgaggtacat aaacctggct cctaaaggct aaaggctaaa tatttgttgg agaaggggca    720
ttggattttg catgaggatg attctgacct gggagggcag gtcagcaggc atctctgttg    780
cacagataga gtgtacaggt ctggagaaca aggagtgggg ggttattgga attccacatt    840
gtttgctgca cgttggattt tgaaatgcta gggaactttg ggagactcat atttctgggc    900
tagaggatct gtggaccaca agatcttttt atgatgacag tagcaatgta tctgtggagc    960
tggattctgg gttgggagtg caaggaaaag aatgtactaa atgccaagac atctatttca   1020
ggagcatgag gaataaaagt tctagtttct ggtctcagag tggtgcaggg atcagggagt   1080
ctcacaatct cctgagtgct ggtgtcttag ggcacactgg gtcttggagt gcaaaggatc   1140
taggcacgtg aggctttgta tgaagaatcg ggatcgtac ccaccccctg tttctgtttc   1200
atcctgggcg tgtctcctct gcctttgtcc cctagatgaa gtctccatga gctacagggc   1260
ctggtgcatc cagggtgatc tagtaattgc agaacagcaa gtactagctc tccctcccct   1320
tccacagctc tgggtgtggg aggggttgt ccagcctcca gcagcatggg gagggccttg   1380
gtcagcctct gggtgccagc agggcagggg cggagtcctg gggaatgaag gttttatagg   1440
gctcctgggg gaggctcccc agccccaagc ttaccacctg cacccggaga gctgtgtcac   1500
catgtgggtc ccggttgtct tcctcaccct gtccgtgacg tggattggtg ctgcacccct   1560
catcctgtct cggattgtgg gaggctggga gtgcgagaag cattcccaac cctggcaggt   1620
gcttgtggcc tctcgtggca gggcagtctg cggcggtgtt ctggtgcacc cccagtgggt   1680
cctcacagct gcccactgca tcaggaacaa aagcgtgatc ttgctgggtc ggcacagcct   1740
gtttcatcct gaagacacag gccaggtatt tcaggtcagc cacagcttcc cacacccgct   1800
ctacgatatg agcctcctga agaatcgatt cctcaggcca ggtgatgact ccagccacga   1860
cctcatgctg ctccgcctgt cagagcctgc cgagctcacg gatgctgtga aggtcatgga   1920
cctgcccacc caggagccag cactggggac cacctgctac gcctcaggct ggggcagcat   1980
tgaaccagag gagttcttga ccccaaagaa acttcagtgt gtggacctcc atgttatttc   2040
caatgacgtg tgtgcgcaag ttcaccctca gaaggtgacc aagttcatgc tgtgtgctgg   2100
acgctggaca gggggcaaaa gcacctgctc gggtgattct ggggccccac ttgtctgtaa   2160
tggtgtgctt caaggtatca cgtcatgggg cagtgaacca tgtgccctgc cgaaaggcc    2220
ttccctgtac accaaggtgg tgcattaccg gaagtggatc aaggacacca tcgtggccaa   2280
cccctgagca cccctatcaa ctccctattg tagtaaactt ggaaccttgg aaatgaccag   2340
gccaagactc aagcctcccc agttctactg acctttgtcc ttaggtgtga ggtccagggt   2400
tgctaggaaa agaaatcagc agacacaggt gtagaccaga gtgtttctta aatggtgtaa   2460
ttttgtcctc tctgtgtcct ggggaatact ggccatgcct ggagacatat cactcaattt   2520
ctctgaggac acagatagga tggggtgtct gtgttatttg tggrtacag agatgaaaga   2580
ggggtgggww ccacactgag agagtggaga gtgacatgtg ctggacactg tccatgaagc   2640
```

-continued

| | |
|---|---|
| actgagcaga agctggaggc acaacgcacc agacactcac agcaaggatg gagctgaaaa | 2700 |
| cataacccac tctgtcctgg aggcactggg aagcctagag aaggctgtga gccaaggagg | 2760 |
| gagggtcttc ctttggcatg ggatggggat gaagtaagga gagggactgg accccctgga | 2820 |
| agctgattca ctatgggggg aggtgtattg aagtcctcca gacaaccctc agatttgatg | 2880 |
| atttcctagt agaactcaca gaaataaaga gctsttatac gtggtttatt ctggtttgtt | 2940 |
| acattgacag gagacacact gaaatcagca aaggaaacag gcatctaagt ggggatgtga | 3000 |
| agaaaacagg gaaaatcttt cagttgtttt ctcccagtgg ggtgttgtgg acagcactta | 3060 |
| aatcacacag aagtgatgtg tgaccttgtg tatgaagtat ttccaactaa ggaagctcac | 3120 |
| ctgagcctta gtgtccagag ttcttattgg gggtctgtag gataggcatg gggtactgga | 3180 |
| atagctgacc ttaacttctc agacctgagg ttcccaagag ttcaagcaga tacagcatgg | 3240 |
| cctagagcct cagatgtaca aaaacaggca ttcatcatga atcgcactgt tagcatgaat | 3300 |
| catctggcac ggcccaaggc cccaggtata ccaaggcact gggccgaat gttccaaggg | 3360 |
| attaaatgtc atctcccagg agttattcaa gggtgagccc tgtacttgga acgttcaggc | 3420 |
| ttt | 3423 |

<210> SEQ ID NO 6
<211> LENGTH: 1261
<212> TYPE: DNA
<213> ORGANISM: Homo sapiens

<400> SEQUENCE: 6

| | |
|---|---|
| gggcgggtc ctggagaatg aaggctttat agggctcctc agggaggccc cccagcccca | 60 |
| aactgcacca cctggccgtg gacacctgtg tcagcatgtg ggacctggtt ctctccatcg | 120 |
| ccttgtctgt ggggtgcact ggtgagattg gggggataaa ggaagggggg cgggttctga | 180 |
| ctcttatgct gaagcccttt tcctcccacc cagtgcccca gcctcgtccc ttcagcccac | 240 |
| agttcagccc agacaatgtg cccctgactc ttccacattg caatagtcct catgcccaca | 300 |
| ctaggtcccc gctccctccc acttacctca gacctttctc tccattgccc agccaaatcc | 360 |
| ctgctcccag ctgctttact aaagagcaag ttcctaggca tctctgtgtt tctctttatg | 420 |
| gggttcaaaa cctttcaagg acctctctcc atgccactgg ttccttggac cctatcactg | 480 |
| ggctgcctcc tgagcccctc agtcctacca cagtctactg acttttccca ttcagctgtg | 540 |
| agcattcaac cctgtcccct ggaccttgac acctggctcc ccaaccctgt cccaggaaac | 600 |
| ccagattcca ccagacactt ccttcttccc ccccgaggct atctggcctg agacaacaaa | 660 |
| tgctgcctcc caccctgagt ctggcactgg gactttcaga actcctcctt ccctgactct | 720 |
| ttgccccaga cccgtcattc aatggctagc ttttccatg ggaagaagaa caacgagcac | 780 |
| ccccaaccac aacggccagt tctctgattc cctaaatccg cacccttttc aaaacctcaa | 840 |
| aaacaaaaca aaacaaaaca aagcaagaaa caactcaggc aaaacttgtt gcttaacctt | 900 |
| ggacatggta aaccatccaa aaccttcctc tcccagcaac taaacctctc cactgggcac | 960 |
| ttaacctttg gtttcttgga acctcttaat ctcttagaac ccacagctgc caccacatgc | 1020 |
| ccttctccca atgtaagacc ccaaatcact ccaaatgacc caacccccaa cccatgcctc | 1080 |
| cttcagatat ttcccatgtc ccctactctg atctctgggg tcagctccgt tctcgagagc | 1140 |
| atgaagcctc ccgacctggt ccagccacca cccgctaac gcagggaata gctacagaat | 1200 |
| tgccagccct cccaggaccc cttgcttgtg tcctggactc ccagtcctgg tcctctgccc | 1260 |
| c | 1261 |

```
<210> SEQ ID NO 7
<211> LENGTH: 104
<212> TYPE: PRT
<213> ORGANISM: Homo sapiens

<400> SEQUENCE: 7

Met Trp Val Pro Val Val Phe Leu Thr Leu Ser Val Thr Trp Ile Gly
1               5                   10                  15

Glu Arg Gly His Gly Trp Gly Asp Ala Gly Glu Gly Ala Ser Pro Asp
            20                  25                  30

Cys Gln Ala Glu Ala Leu Ser Pro Pro Thr Gln His Pro Ser Pro Asp
        35                  40                  45

Arg Glu Leu Gly Ser Phe Leu Ser Leu Pro Ala Pro Leu Gln Ala His
    50                  55                  60

Thr Pro Ser Pro Ser Ile Leu Gln Gln Ser Ser Leu Pro His Gln Val
65                  70                  75                  80

Pro Ala Pro Ser His Leu Pro Gln Asn Phe Leu Pro Ile Ala Gln Pro
                85                  90                  95

Ala Pro Cys Ser Gln Leu Leu Tyr
            100

<210> SEQ ID NO 8
<211> LENGTH: 218
<212> TYPE: PRT
<213> ORGANISM: Homo sapiens

<400> SEQUENCE: 8

Met Lys Asn Arg Gly Ser Tyr Pro Pro Val Ser Val Ser Ser Trp
1               5                   10                  15

Ala Cys Leu Leu Cys Leu Cys Pro Leu Asp Glu Val Ser Met Ser Tyr
            20                  25                  30

Arg Ala Trp Cys Ile Gln Gly Asp Leu Val Ile Ala Glu Gln Gln Val
        35                  40                  45

Leu Ala Leu Pro Pro Leu Pro Gln Leu Trp Val Trp Glu Gly Val Val
    50                  55                  60

Gln Pro Pro Ala Ala Trp Gly Pro Trp Ser Ala Ser Gly Cys Gln
65                  70                  75                  80

Gln Gly Arg Gly Gly Val Leu Gly Asn Glu Gly Phe Ile Gly Leu Leu
                85                  90                  95

Gly Glu Ala Pro Gln Pro Gln Ala Tyr His Leu His Pro Glu Ser Cys
            100                 105                 110

Val Thr Met Trp Val Pro Val Val Phe Leu Thr Leu Ser Val Thr Trp
        115                 120                 125

Ile Gly Glu Arg Gly His Gly Trp Gly Asp Ala Gly Glu Gly Ala Ser
    130                 135                 140

Pro Asp Cys Gln Ala Glu Ala Leu Ser Pro Pro Thr Gln His Pro Ser
145                 150                 155                 160

Pro Asp Arg Glu Leu Gly Ser Phe Leu Ser Leu Pro Ala Pro Leu Gln
                165                 170                 175

Ala His Thr Pro Ser Pro Ser Ile Leu Gln Gln Ser Ser Leu Pro His
            180                 185                 190

Gln Val Pro Ala Pro Ser His Leu Pro Gln Asn Phe Leu Pro Ile Ala
        195                 200                 205

Gln Pro Ala Pro Cys Ser Gln Leu Leu Tyr
    210                 215
```

<210> SEQ ID NO 9
<211> LENGTH: 218
<212> TYPE: PRT
<213> ORGANISM: Homo sapiens

<400> SEQUENCE: 9

Met Lys Asn Arg Gly Ser Tyr Pro Pro Val Ser Val Ser Ser Trp
1               5                   10                  15

Ala Cys Leu Leu Cys Leu Cys Pro Leu Asp Glu Val Ser Met Ser Tyr
            20                  25                  30

Arg Ala Trp Cys Ile Gln Gly Asp Leu Val Ile Ala Glu Gln Gln Val
        35                  40                  45

Leu Ala Leu Pro Pro Leu Pro Gln Leu Trp Val Trp Glu Gly Val Val
    50                  55                  60

Gln Pro Pro Ala Ala Trp Gly Pro Trp Ser Ala Ser Gly Cys Gln
65                  70                  75                  80

Gln Gly Arg Gly Gly Val Leu Gly Asn Glu Gly Phe Ile Gly Leu Leu
                85                  90                  95

Gly Glu Ala Pro Gln Pro Gln Ala Tyr His Leu His Pro Glu Ser Cys
            100                 105                 110

Val Thr Met Trp Val Pro Val Val Phe Leu Thr Leu Ser Val Thr Trp
        115                 120                 125

Ile Gly Glu Arg Gly His Gly Trp Gly Asp Ala Gly Glu Gly Ala Ser
    130                 135                 140

Pro Asp Cys Gln Ala Glu Ala Leu Ser Pro Pro Thr Gln His Pro Ser
145                 150                 155                 160

Pro Asp Arg Glu Leu Gly Ser Phe Leu Ser Leu Pro Ala Pro Leu Gln
                165                 170                 175

Ala His Thr Pro Ser Pro Ser Ile Leu Gln Gln Ser Ser Leu Pro His
            180                 185                 190

Gln Val Pro Ala Pro Ser His Leu Pro Gln Asn Phe Leu Pro Ile Ala
        195                 200                 205

Gln Pro Ala Pro Cys Ser Gln Leu Leu Tyr
    210                 215

<210> SEQ ID NO 10
<211> LENGTH: 183
<212> TYPE: PRT
<213> ORGANISM: Homo sapiens

<400> SEQUENCE: 10

Met Lys Asn Arg Gly Ser Tyr Pro Pro Val Ser Val Ser Ser Trp
1               5                   10                  15

Ala Cys Leu Leu Cys Leu Cys Pro Leu Asp Glu Val Ser Met Ser Tyr
            20                  25                  30

Arg Ala Trp Cys Ile Gln Gly Asp Leu Val Ile Ala Glu Gln Gln Val
        35                  40                  45

Leu Ala Leu Pro Pro Leu Pro Gln Leu Trp Val Trp Glu Gly Val Val
    50                  55                  60

Gln Pro Pro Ala Ala Trp Gly Pro Trp Ser Ala Ser Gly Cys Gln
65                  70                  75                  80

Gln Gly Arg Gly Gly Val Leu Gly Asn Glu Gly Phe Ile Gly Leu Leu
                85                  90                  95

Gly Glu Ala Pro Gln Pro Gln Ala Tyr His Leu His Pro Glu Ser Cys
            100                 105                 110

```
Val Thr Met Trp Val Pro Val Phe Leu Thr Leu Ser Val Thr Trp
        115                 120                 125
Ile Gly Glu Arg Gly His Gly Trp Gly Asp Ala Gly Glu Gly Ala Ser
    130                 135                 140
Pro Asp Cys Gln Ala Glu Ala Leu Ser Pro Pro Thr Gln His Pro Ser
145                 150                 155                 160
Pro Asp Arg Glu Leu Gly Ser Phe Leu Ser Leu Pro Ala Pro Leu Gln
                165                 170                 175
Leu Pro Ala Pro Ser Cys Leu
            180

<210> SEQ ID NO 11
<211> LENGTH: 375
<212> TYPE: PRT
<213> ORGANISM: Homo sapiens

<400> SEQUENCE: 11

Met Lys Asn Arg Gly Ser Tyr Pro Pro Val Ser Val Ser Ser Trp
1               5                   10                  15
Ala Cys Leu Leu Cys Leu Cys Pro Leu Asp Glu Val Ser Met Ser Tyr
                20                  25                  30
Arg Ala Trp Cys Ile Gln Gly Asp Leu Val Ile Ala Glu Gln Gln Val
            35                  40                  45
Leu Ala Leu Pro Pro Leu Pro Gln Leu Trp Val Trp Glu Gly Val Val
        50                  55                  60
Gln Pro Pro Ala Ala Trp Gly Gly Pro Trp Ser Ala Ser Gly Cys Gln
65                  70                  75                  80
Gln Gly Arg Gly Gly Val Leu Gly Asn Glu Gly Phe Ile Gly Leu Leu
                85                  90                  95
Gly Glu Ala Pro Gln Pro Gln Ala Tyr His Leu His Pro Glu Ser Cys
                100                 105                 110
Val Thr Met Trp Val Pro Val Phe Leu Thr Leu Ser Val Thr Trp
        115                 120                 125
Ile Gly Ala Ala Pro Leu Ile Leu Ser Arg Ile Val Gly Gly Trp Glu
    130                 135                 140
Cys Glu Lys His Ser Gln Pro Trp Gln Val Leu Val Ala Ser Arg Gly
145                 150                 155                 160
Arg Ala Val Cys Gly Gly Val Leu Val His Pro Gln Trp Val Leu Thr
                165                 170                 175
Ala Ala His Cys Ile Arg Asn Lys Ser Val Ile Leu Leu Gly Arg His
                180                 185                 190
Ser Leu Phe His Pro Glu Asp Thr Gly Gln Val Phe Gln Val Ser His
            195                 200                 205
Ser Phe Pro His Pro Leu Tyr Asp Met Ser Leu Leu Lys Asn Arg Phe
        210                 215                 220
Leu Arg Pro Gly Asp Asp Ser Ser His Asp Leu Met Leu Arg Leu
225                 230                 235                 240
Ser Glu Pro Ala Glu Leu Thr Asp Ala Val Lys Val Met Asp Leu Pro
                245                 250                 255
Thr Gln Glu Pro Ala Leu Gly Thr Thr Cys Tyr Ala Ser Gly Trp Gly
                260                 265                 270
Ser Ile Glu Pro Glu Glu Phe Leu Thr Pro Lys Lys Leu Gln Cys Val
            275                 280                 285
Asp Leu His Val Ile Ser Asn Asp Val Cys Ala Gln Val His Pro Gln
```

```
      290                 295                 300
Lys Val Thr Lys Phe Met Leu Cys Ala Gly Arg Trp Thr Gly Gly Lys
305                 310                 315                 320

Ser Thr Cys Ser Gly Asp Ser Gly Gly Pro Leu Val Cys Asn Gly Val
                325                 330                 335

Leu Gln Gly Ile Thr Ser Trp Gly Ser Glu Pro Cys Ala Leu Pro Glu
                340                 345                 350

Arg Pro Ser Leu Tyr Thr Lys Val Val His Tyr Arg Lys Trp Ile Lys
            355                 360                 365

Asp Thr Ile Val Ala Asn Pro
        370                 375

<210> SEQ ID NO 12
<211> LENGTH: 141
<212> TYPE: PRT
<213> ORGANISM: Homo sapiens

<400> SEQUENCE: 12

Met Trp Asp Leu Val Leu Ser Ile Ala Leu Ser Val Gly Cys Thr Gly
1               5                   10                  15

Glu Ile Gly Gly Ile Lys Glu Gly Gly Arg Val Leu Thr Leu Met Leu
            20                  25                  30

Lys Pro Phe Ser Ser His Pro Val Pro Gln Pro Arg Pro Phe Ser Pro
        35                  40                  45

Gln Phe Ser Pro Asp Asn Val Pro Leu Thr Leu Pro His Cys Asn Ser
    50                  55                  60

Pro His Ala His Thr Arg Ser Pro Leu Pro Thr Tyr Leu Arg Pro
65                  70                  75                  80

Phe Ser Pro Leu Pro Ser Gln Ile Pro Ala Pro Ser Cys Phe Thr Lys
                85                  90                  95

Glu Gln Val Pro Arg His Leu Cys Val Ser Leu Tyr Gly Val Gln Asn
            100                 105                 110

Leu Ser Arg Thr Ser Leu His Ala Thr Gly Ser Leu Asp Pro Ile Thr
        115                 120                 125

Gly Leu Pro Pro Glu Pro Leu Ser Pro Thr Thr Val Tyr
    130                 135                 140

<210> SEQ ID NO 13
<211> LENGTH: 10574
<212> TYPE: DNA
<213> ORGANISM: Homo sapiens

<400> SEQUENCE: 13
aagcttctag ttttcttttc ccggtgacat cgtggaaagc actagcatct ctaagcaatg      60
atctgtgaca atattcacag tgtaatgcca tccagggaac tcaactgagc cttgatgtcc     120
agagattttt gtgttttttt ctgagactga gtctcgctct gtgccaggct ggagtgcagt     180
ggtgcaacct tggctcactg caagctccgc ctcctgggtt cacgccattc tcctgcctca     240
gcctcctgag tagctgggac tacaggcacc cgccaccacg cctggctaat ttttttgtat     300
ttttagtaga gatggggttt cactgtgtta gccaggatgg tctcagtctc ctgacctcgt     360
gatctgccca ccttggcctc ccaaagtgct gggatgacag gcgtgagcca ccgcgcctgg     420
ccgatatcca gagattttt ggggggctcc atcacacaga catgttgact gtcttcatgg     480 ttgacttta gtatccagcc cctctagaaa tctagctgat atagtgtggc tcaaaacctt     540
cagcacaaat cacaccgtta gactatctgg tgtggcccaa accttcaggt gaacaaaggg     600
```

-continued

```
actctaatct ggcaggatat tccaaagcat tagagatgac ctcttgcaaa gaaaagaaa      660 tggaaaagaa aaagaaagaa aggaaaaaaa aaaaaaaaaa gagatgacct ctcaggctct     720
gaggggaaac gcctgaggtc tttgagcaag gtcagtcctc tgttgcacag tctccctcac     780 aggtcattg tgacgatcaa atgtggtcac gtgtatgagg caccagcaca tgcctggctc      840
tggggagtgc cgtgtaagtg tatgcttgca ctgctgaatg cttgggatgt gtcagggatt     900
atcttcagca cttacagatg ctcatctcat cctcacagca tcactatggg atgggtatta    960
ctggcctcat tgatggaga aagtggctgt ggctcagaaa ggggggacca ctagaccagg      1020
gacactctgg atgctgggga ctccagagac catgaccact caccaactgc agagaaatta    1080
attgtggcct gatgtccctg tcctggagag ggtggaggtg gaccttcact aacctcctac    1140
cttgaccctc tcttttaggg ctctttctga cctccaccat ggtactagga ccccattgta    1200
ttctgtaccc tcttgactct atgaccccca ctgcccactg catccagctg ggtcccctcc    1260
tatctctatt cccagctggc cagtgcagtc tcagtgccca cctgtttgtc agtaactctg    1320
aaggggctga cattttactg acttgcaaac aaataagcta actttccaga gttttgtgaa    1380
tgctggcaga gtccatgaga ctcctgagtc agaggcaaag gcttttactg ctcacagctt    1440
agcagacagc atgaggttca tgttcacatt agtacacctt gccccccca aatcttgtag     1500 ggtgaccaga gcagtctagg tggatgctgt gcagaagggg tttgtgccac tggtgagaaa    1560
cctgagatta ggaatcctca atcttatact gggacaactt gcaaacctgc tcagcctttg    1620
tctctgatga agatattatc ttcatgatct tggattgaaa acagacctac tctggaggaa    1680
catattgtat cgattgtcct tgacagtaaa caaatctgtt gtaagagaca ttatctttat    1740
tatctaggac agtaagcaag cctggatctg agagagatat catcttgcaa ggatgcctgc    1800
tttacaaaca tccttgaaac aacaatccag aaaaaaaaag gtgttgctgt ctttgctcag    1860
aagacacaca gatacgtgac agaaccatgg agaattgcct cccaacgctg ttcagccaga    1920
gccttccacc cttgtctgca ggacagtctc aacgttccac cattaaatac ttcttctatc    1980
acatcctgct tctttatgcc taaccaaggt tctaggtccc gatcgactgt gtctggcagc    2040
actccactgc caaacccaga ataaggcagc gctcaggatc ccgaaggggc atggctgggg    2100
atcagaactt ctgggtttga gtgaggagtg ggtccaccct cttgaatttc aaaggaggaa    2160
gaggctggat gtgaaggtac tggggaggg aaagtgtcag ttccgaactc ttaggtcaat     2220
gagggaggag actggtaagg tcccagctcc cgaggtactg atgtgggaat ggcctaagaa    2280
tctcatatcc tcaggaagaa ggtgctggaa tcctgagggg tagagttctg ggtatatttg    2340
tggcttaagg ctcttttggcc cctgaaggca gaggctggaa ccattaggtc cagggtttgg   2400
ggtgatagta atgggatctc ttgattcctc aagagtctga ggatcgaggg ttgcccattc    2460
ttccatcttg ccacctaatc cttactccac ttgagggtat caccagccct tctagctcca    2520
tgaaggtccc ctgggcaagc acaatctgag catgaaagat gccccagagg ccttgggtgt    2580
catccactca tcatccagca tcacactctg agggtgtggc cagcaccatg acgtcatgtt    2640
gctgtgacta tccctgcagc gtgcctctcc agccacctgc caaccgtaga gctgcccatc    2700
ctcctctggt gggagtggcc tgcatggtgc caggctgagg cctagtgtca gacagggagc    2760
ctggaatcat agggatccag gactcaaaag tgctagagaa tggccatatg tcaccatcca    2820
tgaaatctca agggcttctg ggtggagggc acagggacct gaacttatgg tttcccaagt    2880
ctattgctct cccaagtgag tctcccagat acgaggcact gtgccagcat cagccttatc    2940
```

-continued

```
tccaccacat cttgtaaaag gactacccag ggccctgatg aacaccatgg tgtgtacagg      3000 agtaggggt ggaggcacgg actcctgtga ggtcacagcc aagggagcat catcatgggt      3060
ggggaggagg caatggacag gcttgagaac ggggatgtgg ttgtatttgg ttttctttgg      3120
ttagataaag tgctgggtat aggattgaga gtggagtatg aagaccagtt aggatggagg      3180
atcagattgg agttgggtta gataaagtgc tgggtatagg attgagagtg gagtatgaag      3240
accagttagg atggaggatc agattggagt tgggttagag atggggtaaa attgtgctcc      3300
ggatgagttt gggattgaca ctgtggaggt ggtttgggat ggcatggctt tgggatggaa      3360
atagatttgt tttgatgttg gctcagacat ccttgggat tgaactgggg atgaagctgg       3420
gtttgatttt ggaggtagaa gacgtggaag tagctgtcag atttgacagt ggccatgagt      3480
tttgtttgat ggggaatcaa acaatggggg aagacataag ggttggcttg ttaggttaag      3540
ttgcgttggg ttgatgggt cggggctgtg tataatgcag ttggattggt ttgtattaaa       3600
ttgggttggg tcaggttttg gttgaggatg agttgaggat atgcttgggg acaccggatc      3660
catgaggttc tcactggagt ggagacaaac ttcctttcca ggatgaatcc agggaagcct      3720
taattcacgt gtaggggagg tcaggccact ggctaagtat atccttccac tccagctcta      3780
agatggtctt aaattgtgat tatctatatc cacttctgtc tccctcactg tgcttggagt      3840
ttacctgatc actcaactag aaacagggga agattttatc aaattctttt ttttttttt      3900 ttttttttga gacagagtct cactctgttg cccaggctgg agtgcagtgg cgcagtctcg      3960
gctcactgca acctctgcct cccaggttca agtgattctc ctgcctcagc ctcctgagtt      4020
gctgggatta caggcatgca gcaccatgcc cagctaattt ttgtattttt agtagagatg      4080
gggtttcacc aatgtttgcc aggctggcct cgaactcctg acctggtgat ccacctgcct      4140
cagcctccca agtgctggg attacaggcg tcagccaccg cgcccagcca cttttgtcaa       4200
attcttgaga cacagctcgg gctggatcaa gtgagctact ctggttttat tgaacagctg      4260
aaataaccaa cttttggaa attgatgaaa tcttacggag ttaacagtgg aggtaccagg       4320
gctcttaaga gttcccgatt ctcttctgag actacaaatt gtgattttgc atgccacctt      4380
aatctttttt tttttttttt taaatcgagg tttcagtctc attctatttc ccaggctgga      4440
gttcaatagc gtgatcacag ctcactgtag ccttgaactc ctggccttaa gagattctcc      4500
tgcttcggtc tcccaatagc taagactaca gtagtccacc accatatcca gataatttt     4560 aaatttttg gggggccggg cacagtggct cacgcctgta atcccaacac catgggaggc       4620
tgagatgggt ggatcacgag gtcaggagtt tgagaccagc ctgaccaaca tggtgaaact      4680
ctgtctctac taaaaaaaaa aaaaatagaa aaattagccg ggcgtggtgg cacacggcac      4740
ctgtaatccc agctactgag gaggctgagg caggagaatc acttgaaccc agaaggcaga      4800
ggttgcaatg agccgagatt gcgccactgc actccagcct gggtgacaga gtgagactct      4860
gtctcaaaaa aaaaaatttt ttttttttt tttgtagaga tggatcttgc tttgtttctc       4920
tggttggcct tgaactcctg gcttcaagtg atcctcctac cttggcctcg gaaagtgttg      4980
ggattacagg cgtgagccac catgactgac ctgtcgttaa tcttgaggta cataaacctg      5040
gctcctaaag gctaaaggct aaatatttgt tggagaaggg gcattggatt ttgcatgagg      5100
atgattctga cctgggaggg caggtcagca ggcatctctg ttgcacagat agagtgtaca      5160
ggtctggaga acaaggagtg gggggttatt ggaattccac attgtttgct gcacgttgga      5220
ttttgaaatg ctagggaact ttgggagact catatttctg ggctagagga tctgtggacc      5280
acaagatctt tttatgatga cagtagcaat gtatctgtgg agctggattc tgggttggga      5340
```

-continued

```
gtgcaaggaa aagaatgtac taaatgccaa gacatctatt tcaggagcat gaggaataaa    5400
agttctagtt tctggtctca gagtggtgca gggatcaggg agtctcacaa tctcctgagt    5460
gctggtgtct tagggcacac tgggtcttgg agtgcaaagg atctaggcac gtgaggcttt    5520
gtatgaagaa tcgggatcg tacccacccc ctgtttctgt ttcatcctgg gcatgtctcc    5580
tctgcctttg tccctagat gaagtctcca tgagctacag gcctggtgc atccagggtg     5640
atctagtaat tgcagaacag caagtgctag ctctccctcc ccttccacag ctctgggtgt    5700
gggaggggt tgtccagcct ccagcagcat ggggagggcc ttggtcagcc tctgggtgcc     5760
agcagggcag gggcggagtc ctggggaatg aaggttttat agggctcctg ggggaggctc    5820
cccagcccca agcttaccac ctgcacccgg agagctgtgt caccatgtgg gtcccggttg    5880
tcttcctcac cctgtccgtg acgtggattg gtgagagggg ccatggttgg ggggatgcag    5940
gagagggagc cagccctgac tgtcaagctg aggctctttc cccccaacc cagcacccca     6000
gcccagacag ggagctgggc tcttttctgt ctctcccagc cccactccaa gcccataccc    6060
ccagcccctc catattgcaa cagtcctcac tcccacacca gtccccgct ccctcccact     6120
taccccagaa ctttctcccc atttgcccag ccagctccct gctcccagct gctttactaa    6180
agggaagtt cctgggcatc tccgtgtttc tctttgtggg gctcaaaacc tccaaggacc     6240
tctctcaatg ccattggttc cttggaccgt atcactggtc cacctcctga gcccctcaat    6300
cctatcacag tctactgact tttccattca gctgtgagtg cccaaccta tcccagagac     6360
cttgatgctt ggcctcccaa tcttgcccta ggatacccag atgccaacca gacacctcct    6420
tcttcctagc caggctatct ggctgagaca acaaatgggt ccctcagtct ggcaatggga    6480
ctctgagaac tcctcattcc ctgactctta gccccagact cttcattcag tggcccacat    6540
tttccttagg aaaaacatga gcatccccag ccacaactgc cagctctctg attccccaaa    6600
tctgcatcct tttcaaaacc taaaacaaa agaaaaaca aataaaacaa aaccaactca     6660
gaccagaact gttttctcaa cctgggactt cctaaacttt ccaaaacctt cctcttccag    6720
caactgaacc tcccgataag gcacttatcc ctggttccta gcaccgctta tccctcaga     6780
atccacaact tgtaccaagt ttcccttctc ccagtccaag accccaaatc accacaaagg    6840
acccaatccc cagactcaag atatggtctg ggctgtcttt gtgtctccta ccctgatccc    6900
tgggttcaac tctgtcccag agcatgaagc ctctccacca gcaccagcca caacctgca     6960
aacctaggga agattgacag aattcccagc ctttcccagc tcccccctgcc catgtcccag    7020
gactcccagc cttggttctc tgcccccgtg tcttttcaaa cccacatcct aaatccatct    7080
cctatccgag tcccccagtt cctcctgtca accctgattc cctgatcta gcacccctc     7140
tgcaggtgct gcacccctca tcctgtctcg gattgtggga ggctgggagt gcgagaagca    7200
ttcccaaccc tggcaggtgc ttgtggcctc tcgtggcagg gcagtctgcg gcggtgttct    7260
ggtgcacccc cagtgggtcc tcacagctgc ccactgcatc aggaagtgag tagggcctg    7320
gggtctgggg agcaggtgtc tgtgtccaga ggaataacag ctgggcattt tccccaggat    7380
aacctctaag gccagccttg ggactggggg agagagggaa agttctggtt caggtcacat    7440
ggggaggcag ggttgggget ggaccaccct cccatggct gctgggtct ccatctgtgt      7500
tcctctatgt ctctttgtgt cgctttcatt atgtctcttg gtaactggct tcggttgtgt    7560
ctctccgtgt gactattttg ttctctctct ccctctcttc tctgtcttca gtctccatat    7620
ctccccctct ctctgtcctt ctctggtccc tctctagcca gtgtgtctca ccctgtatct    7680
```

```
ctctgccagg ctctgtctct cggtctctgt ctcacctgtg ccttctccct actgagcaca    7740
cgcatgggat gggcctgggg ggaccctgag aaaaggaagg gctttggctg ggcgcggtgg    7800
ctcacacctg taatcccagc actttgggag gccaaggcag gtagatcacc tgaggtcagg    7860
agttcgagac cagcctggcc aactggtgaa accccatctc tactaaaaat acaaaaaatt    7920
agccaggcgt ggtcggcgca tgcctgtagt cccagctact caggaggctg agggaggaga    7980
attgcttgaa cctgggaggt ggaggttgca gtgagccgag acgtgccact gcactccagc    8040
ctgggtgaca gagtgagact ccgcctcaaa aaaaaaaaaa aaaaaaaaga aaagaaaaga    8100
aaagaaaagg aagtgtttta tccctgatgt gtgtgggtat gagggtatga gagggcccct    8160
ctcactccat tccttctcca ggacatccct ccactcttgg gagacacaga gaagggctgg    8220
ttcagctgga gctgggaggg gcaattgagg gaggaggaag gagaaggggg aaggaaaaca    8280
gggtatgggg gaaggaccc tggggagcga agtggaggat acaaccttgg gcctgcaggc      8340
caggctacct acccacttgg aaacccacgc caaagccgca tctacagctg agccactctg    8400
aggcctcccc tccccagcgg tccccactca gctccaaagt ctctctccct tttctctccc    8460
acactctatc atccccgga ttcctctcta cttggttctc attcttcctt tgacttcctg      8520
cttccctttc tcattcatct gtttctcact ttctgcctgg ttttgttctt ctctctctct    8580
ttctctggcc catgtctgtt tctctatgtt tctgtctttt ctttctcatc ctgtgtattt    8640
tcggctcacc ttgtttgtca ctgttctccc ctctgccctt tcattctctc tgtccttta     8700
ccctcttcct ttttcccttg gtttctctca gtttctgtat ctgcccttca ccctctcaca    8760
ctgctgtttc ccaactcgtt gtctgtattt ttggcctgaa catgtgtctt ccccaaccct    8820
gtgttttct cactgtttct ttttctcttt tggagcctcc tccttgctcc tctgtccctt     8880
ctctctttcc ttatcatcct cgctcctcat tcctgcgtct gcttcctccc cagcaaaagc    8940
gtgatcttgc tgggtcggca cagcctgttt catcctgaag acacaggcca ggtatttcag    9000
gtcagccaca gcttcccaca cccgctctac gatatgagcc tcctgaagaa tcgattcctc    9060
aggccaggtg atgactccag ccacgacctc atgctgctcc gcctgtcaga gcctgccgag    9120
ctcacggatg ctgtgaaggt catggacctg cccacccagg agccagcact ggggaccacc    9180
tgctacgcct caggctgggg cagcattgaa ccagaggagt gtacgcctgg gccagatggt    9240
gcagccggga gcccagatgc ctgggtctga gggaggaggg gacaggactc ctaggtctga    9300
gggaggaggg ccaaggaacc aggtgggggtc cagcccacaa cagtgttttt tgcctggccc   9360
gtagtcttga ccccaaagaa acttcagtgt gtggacctcc atgttatttc caatgacgtg    9420
tgtgcgcaag ttcaccctca gaaggtgacc aagttcatgc tgtgtgctgg acgctggaca    9480
gggggcaaaa gcacctgctc ggtgagtcat ccctactccc aagatcttga ggggaaaggt    9540
gagtggggac cttaattctg ggctgggggtc tagaagccaa caagcatctg cctccctgc    9600
tccccagctg tagccatgcc acctccccgt gtctcatctc attccctcct tccctcttct    9660
ttgactccct caaggcaata ggttattctt acagcacaac tcatctgttc ctgcgttcag    9720
cacacggtta ctaggcacct gctatgcacc cagcactgcc ctagagcctg acatagcag     9780
tgaacagaca gagagcagcc cctcccttct gtagccccca agccagtgag gggcacaggc    9840
aggaacaggg accacaacac agaaaagctg gagggtgtca ggaggtgatc aggctctcgg    9900
ggagggagaa ggggtgggga gtgtgactgg gaggagacat cctgcagaag gcgggagtga    9960
gcaaacacct gccgcagggg agggggaggc ctgcggcacc tgggggagca gagggaacag    10020
catctggcca ggcctgggag gaggggccta gagggcgtca ggagcagaga ggaggttgcc    10080
```

-continued

```
tggctggagt gaaggatcgg ggcagggtgc gagagggaag aaggacccct cctgcagggc    10140
ctcacctggg ccacaggagg acactgcttt tcctctgagg agtcaggaac tgtggatggt    10200
gctggacaga agcaggacag ggcctggctc aggtgtccag aggctgccgc tggcctccct    10260
atgggatcag actgcaggga gggagggcag cagggatgtg gagggagtga tgatggggct    10320
gacctggggg tggctccagg cattgtcccc acctgggccc ttaccagcc tccctcacag    10380 gctcctggcc ctcagtctct cccctccact ccattctcca cctacccaca gtgggtcatt    10440
ctgatcaccg aactgaccat gccagccctg ccgatggtcc tccatggctc cctagtgccc    10500
tggagaggag gtgtctagtc agagagtagt cctggaaggt ggcctctgtg aggagccacg    10560
gggacagcat cctg                                                      10574
```

<210> SEQ ID NO 14
<211> LENGTH: 262
<212> TYPE: PRT
<213> ORGANISM: Homo sapiens

<400> SEQUENCE: 14

```
Met Trp Val Pro Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Lys Cys Lys Ser Val Ile Leu Leu Gly Arg His Ser
65                  70                  75                  80

Leu Phe His Pro Glu Asp Thr Gly Gln Val Phe Gln Val Ser His Ser
                85                  90                  95

Phe Pro His Pro Leu Tyr Asp Met Ser Leu Leu Lys Asn Arg Phe Leu
            100                 105                 110

Arg Pro Gly Asp Asp Ser Ser His Asp Leu Met Leu Leu Arg Leu Ser
        115                 120                 125

Glu Pro Ala Glu Leu Thr Asp Ala Val Lys Val Met Asp Leu Pro Thr
    130                 135                 140

Gln Glu Pro Ala Leu Gly Thr Thr Cys Tyr Ala Ser Gly Trp Gly Ser
145                 150                 155                 160

Ile Glu Pro Glu Glu Phe Leu Thr Pro Lys Lys Leu Gln Cys Val Asp
                165                 170                 175

Leu His Val Ile Ser Asn Asp Val Cys Ala Gln Val His Pro Gln Lys
            180                 185                 190

Val Thr Lys Phe Met Leu Cys Ala Gly Arg Trp Thr Gly Gly Lys Ser
        195                 200                 205

Thr Cys Ser Gly Asp Ser Gly Gly Pro Leu Val Cys Asn Gly Val Leu
    210                 215                 220

Gln Gly Ile Thr Ser Trp Gly Ser Glu Pro Cys Ala Leu Pro Glu Arg
225                 230                 235                 240

Pro Ser Leu Tyr Thr Lys Val Val His Tyr Arg Lys Trp Ile Lys Asp
                245                 250                 255

Thr Ile Val Ala Asn Pro
            260
```

```
<210> SEQ ID NO 15
<211> LENGTH: 18
<212> TYPE: PRT
<213> ORGANISM: Homo sapiens

<400> SEQUENCE: 15

Met Trp Asp Leu Val Leu Ser Ile Ala Leu Ser Val Gly Cys Thr Gly
1               5                   10                  15

Ala Val

<210> SEQ ID NO 16
<211> LENGTH: 18
<212> TYPE: PRT
<213> ORGANISM: Homo sapiens

<400> SEQUENCE: 16

Cys Gln Ala Glu Leu Ser Pro Pro Thr Gln His Pro Ser Pro Asp Arg
1               5                   10                  15

Glu Leu
```

NUCLEIC ACID AND AMINO ACID SEQUENCES

CROSS-REFERENCE TO RELATED APPLICATIONS

This application is based on and claims the benefit of U.S. Continuation-in-Part application Ser. No. 09/701,238, filed Nov. 27, 2000, now abandoned, which is a §371 of PCT/IL00/00102, filed Feb. 18, 2000, the entire disclosure of each of which is relied upon and incorporated by reference herein.

FIELD OF THE INVENTION

The present invention concerns novel nucleic acid sequences, vectors and host cells containing them, amino acid sequences encoded by said sequences, and antibodies reactive with said amino acid sequences, as well as pharmaceutical compositions comprising any of the above. The present invention further concerns methods for screening for candidate activator or deactivators utilizing said amino acid sequences.

BACKGROUND OF THE INVENTION

Prostate-specific antigen (PSA) is the most important tumor marker for early detection, staging, and monitoring of men with prostate cancer today. PSA testing has appreciable false-positive and false-negative results, particularly in the 2.5–10 ng/ml range. Measurement of the percentage of non-protein-bound (i.e. free) PSA in serum, which is lower in patients with prostate cancer, have been evaluated as a method for increasing the accuracy of PSA testing.

Thus measurement of PSA in serum, has been postulated as having potential clinical utility for increasing the sensitivity and specificity of PSA testing. Cutoff figures are affected by total PSA levels at prostate value. The prevalence rate of cancer in the screened population, depending on age, race, previous biopsy history etc., also influences the screening cutoffs. It has also been postulated that the percentage of free PSA may also correlate with a potential aggressiveness of early-stage prostate cancer. Thus, the level of free PSA may not only be used in order to diagnose prostate cancer, but also to predict the course of development of this cancer, and the patient's prognosis, and decide on a suitable treatment regime.

Human kallikrein-2 gene (termed herein after: "KLK" which is also known as KLK-2) is transcribed from the same locus as the PSA and is also known to be prostate specific. It has been speculated that both PSA and KLK have common expression control such as common enhancer and/or promoter and both function as serine proteases.

GLOSSARY

In the following description and claims use will be made, at times, with a variety of terms, and the meaning of such terms as they should be construed in accordance with the invention is as follows:

"Prostate specific antigen (PSA) variant"—the sequence shown in any one of SEQ ID NO: 1 to SEQ ID NO: 6, sequences having at least 70% identity to said sequence and fragments of the above sequences of least 20 b.p. long. SEQ ID NO: 1 to ID NO:5 are nucleic acid sequences which resulted from alternative splicing of the native and known PSA sequence appearing in HSPSAR and HUMPSANTIG (GenBank Acc. X05332 and M24543, respectively). It should be emphasized that the PSA variants of the invention are naturally occurring sequences resulting from the alternative splicing of the RNA transcribed from the PSA gene and not merely truncated or mutated forms of the gene. SEQ ID NO: 6 is an alternative splice variant of the human kallikrein-2 gene (KLK-2) appearing in GenBank as KLK2 under Accession Number NM_005551.

SEQ ID NO: 1—(PSAL_0): The nucleic acid sequence starting in position 4364 of the HUMPSANTIG up to position 7305, then a different sequence. The coded peptide (SEQ ID NO:7) starting identically to the original PSA for 16 aa, then a different sequence which is trancribed from the PSA intron between exons 1 and 2.

SEQ ID NO:2—(PSAL_1): Nucleic acid sequence identical to SEQ 1.

Peptide (SEQ ID NO: 8)—Starting in a Methionine 114 aa upstream from the original PSA, and has the same 16 aa identity and 3' end as PSAL_0.

SEQ ID NO:3—(PSAL_2): Nucleic acid sequence which starts in same place as PSAL_0 but goes up to position 6336 of the HUMPSANTIG, then continues in a different sequence. Peptide (SEQ ID NO: 9)—Identical to PSAL_1 peptide.

SEQ ID NO: 4—(PSAL_5): Nucleic acid sequence which starts in same place as PSAL_0, goes up to position 6069 of HUMPSANTIG and end there (original intron). Peptide (SEQ ID NO:10)—Has same starting place as PSAL_1, the same 16 aa identity to PSA, then a different intron region translated.

SEQ ID NO: 5—(PSAL_6): Nucleic acid sequence starts in the same place as PSAL_0, goes up to position 5913 of HUMPSANTIG, then enter the original PSA exon # 2 and continues. Peptide (SEQ ID NO:11) has same starting place as PSAL_1, then enters the same identity region and continues as the original PSA until the end.

SEQ ID NO:6 is a splice variant of the KLK-2 that includes coding region from the original KLK-2 intron between exons 1 and 2. The term of "PSA variant" in the context of the present invention concerns splice variants of the known PSA gene as well as splice variants of the KLK-2 gene, which is also known to code for antigens specific to the prostate.

"Prostate specific antigen variant product (PSA variant product)—also referred at times as the "PSA variant protein" or "PSA variant polypeptide"—an amino acid sequence coded by said PSA variant nucleic acid sequence. The amino acid sequence may be a peptide, a protein, as well as peptides or proteins having chemically modified amino acids (see below) such as a glycopeptide or glycoprotein. An example of a PSA variant product is shown in any one of SEQ ID NO: 7 to SEQ ID NO: 12, and includes also analogues of said sequences in which one or more amino acids has been added, deleted, substituted (see below) or chemically modified (see below) as well as fragments of this sequence having at least 10 amino acids. The products may be membrane associated or present in a free form in body fluids, for example in the serum.

"Nucleic acid sequence"—a sequence composed of DNA nucleotides, RNA nucleotides or a combination of both types and may includes natural nucleotides, chemically modified nucleotides and synthetic nucleotides.

"Amino acid sequence"—a sequence composed of any one of the 20 naturally appearing amino acids, amino acids which have been chemically modified (see below), or composed of synthetic amino acids.

"Fragment of PSA variant product" a sequence which is the same as part of but not all of the amino acid sequence of the PSA variant product.

"Fragments of PSA variant nucleic acid sequence" a continuous portion, preferably of about 20 nucleic acid sequences of the PSA variant nucleic acid sequence (see below), which sequence does not appear in the original PSA.

"Conservative substitution"—refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. [Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Chemically modified"—when referring to the product of the invention, means a product (protein) where at least one of its amino acid resides is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiquitination, or any similar process.

"Biologically active"—refers to a PSA variant product which has the ability to serve as a marker of cancer, of predisposition to cancer, or of malignancy of a tumor.

"Immunologically active" defines the capability of a natural, recombinant or synthetic PSA variant product, or any fragment thereof, to induce a specific immune response in appropriate animals or cells and to bind with specific antibodies. Thus, for example, a biologically active fragment of PSA variant product denotes a fragment which retains some or all of the biological properties of the PSA variant product, e.g the ability to serve as a marker for prostate cancer; an immunologically active fragment is a fragment which can bind specific anti-PSA variant product antibodies or "distinguishing antibodies" (see below) which can elicit an immune response which will generate such antibodies or cause proliferation of PSA variant product-specific immune cells. The fragment will also be denoted hereinafter as "distinguishing amino acid sequence".

"Optimal alignment"—is defined as an alignment giving the highest percent identity score. Such alignment can be performed using a variety of commercially available sequence analysis programs, such as the local alignment program LALIGN using a ktup of 1, default parameters and the default PAM. A preferred alignment is the one performed using the CLUSTAL-W program from MacVector (TM), operated with an open gap penalty of 10.0, an extended gap penalty of 0.1, and a BLOSUM similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence).

"Having at least X% identity"—with respect to two amino acid or nucleic acid sequence sequences, refers to the percentage of residues that are identical in the two sequences when the sequences are optimally aligned. Thus, 90% amino acid sequence identity means that 90% of the amino acids in two or more optimally aligned polypeptide sequences are identical.

"Isolated nucleic acid molecule having an PSA variant nucleic acid sequence"—is a nucleic acid molecule that includes the coding PSA variant nucleic acid sequences. Said isolated nucleic acid molecule may include the PSA variant nucleic acid sequence as an independent insert; may include the PSA variant nucleic acid sequence fused to an additional coding sequences, encoding together a fusion protein in which the PSA variant coding sequence is the dominant coding sequence (for example, the additional coding sequence may code for a signal peptide); the PSA variant nucleic acid sequence may be in combination with non-coding sequences, e.g., introns or control elements, such as promoter and terminator elements or 5' and/or 3' untranslated regions, effective for expression of the coding sequence in a suitable host; or may be a vector in which the PSA variant protein coding sequence is a heterologous.

"Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

"Antibody"—refers to IgG, IgM, IgD, IgA, and IgG antibody. The definition includes polyclonal antibodies or monoclonal antibodies. This term refers to whole antibodies or fragments of the antibodies comprising the antigen-binding domain of the anti-PSA variant product antibodies, e.g. antibodies without the Fc portion, single chain antibodies, fragments consisting of essentially only the variable, antigen-binding domain of the antibody, etc.

"Distinguishing antibody"—an antibody capable of binding only to the novel PSA variant product of the invention while not binding to the original PSA product, i.e. an antibody recognizing an additional amino acid sequence which appears only in the variant product of the invention and not in the original PSA sequence. This term may also refer at times to antibodies which binda sequence present in the original PSA and not present in the PSA variant product.

"Distinguishing amino acid sequence"—an amino acid sequence of at least two amino acids which are present only in the PSA variant of the invention and not in the original PSA of which are used to prepare the above distinguishing antibodies.

"Activator"—as used herein, refers to a molecule which mimics the effect of the natural PSA variant product or at times even increases or prolongs the duration of the biological activity of said product, as compared to that induced by the natural product. The mechanism may be by binding to the PSA variant receptor, by prolonging the lifetime of the PSA variant, by increasing the activity of the PSA variant on its target, by increasing the affinity of PSA variant to its receptor, etc. Activators may be polypeptides, nucleic acids, carbohydrates, lipids, or derivatives thereof, or any other molecules which can bind to and activate the PSA variant product.

"Deactivator"—refers to a molecule which modulates the activity of the PSA variant product in an opposite manner to that of the activator, by decreasing or shortening the duration of the biological activity of the PSA variant product. This may be done by blocking the binding of the PSA variant to its receptor, competitive or non competitive inhibitor, by causing rapid degradation of the PSA variant, etc. Deactivators may be polypeptides, nucleic acids, carbohydrates, lipids, or derivatives thereof, or any other molecules which bind to and modulate the activity of said product.

"Treating a disease"—refers to administering a therapeutic substance effective to ameliorate symptoms associated with a disease, to lessen the severity or cure the disease, or to prevent the disease from occurring. In the context of the invention the disease is typically cancer and in particular prostate cancer.

"Detection"—refers to a method of detection of a disease, such as prostate cancer. May be detection of an active disease or detection of a predisposition to a disease. By another alternative the detection may be capable of distinguishing between benign and malignant conditions. This term may also be used in connection with a method for evaluating the aggressiveness of a malignant state in order to correctly predict the prognosis of the patient, and in that case the detection may be used to assess the stage of the tumor.

"Probe"—the PSA variant nucleic acid sequence, or a sequence (including fragments) complementary therewith, when used to detect presence of other similar sequences in a sample. The detection is carried out by identification of hybridization complexes between the probe and the assayed sequence. The probe may be attached to a solid support or to a detectable label. The probe may be a fragment of any one of the SEQ ID NO: 1 to SEQ ID NO: 6 (including a fragment of the non-coding region) which is of sufficient length to hybridize to the PSA variants at a level significantly different from the binding to the original PSA sequence. The probes may also be used to detect the polymorphisms described in the nucleic acid for the purpose of determining predisposition to cancer, especially prostate cancer in healthy individuals, and for detecting loss of heterozigosity in prostate tissues as part of a malignant transformation. The probes may be used in any method of performing this assay, including primer-specific PCR, allele-specific oligonucleotide assay, restriction fragment length differences, and mini-sequencing.

"Targeting"—directing a compound or drug to a desired cell population. Targeting is carried out by conjugating to the compound or drug an agent capable of binding specifically to the desired cell population, while not binding to non-desired cell populations. A specific example is targeting cytotoxic drugs directed only to tumor cells, more specifically directed to prostate tumor cells, for example, by conjugating the drug to an antibody of the invention.

"Original PSA sequence"—the known sequence of PSA as appears in GenBank HSPSAR locus and Acc # X05332, as well as to the known KLK-2 sequence as appears in GenBank KLK2 (NM_005551).

SUMMARY OF THE INVENTION

The present invention provides by its first aspect, a novel isolated nucleic acid molecule comprising or consisting of the coding sequence of any one of SEQ ID NO: 1 to SEQ ID NO: 6, fragments of said coding sequence having at least 20 nucleic acids, or a molecule comprising a sequence having at 90% identity to any one of SEQ ID NO:1 to SEQ ID NO: 6. Preferably, the fragments should be such that they comprise sequences present in the PSA variants of the invention and not a sequence present in the original PSA (the term "original PSA" also includes the KLK-2 sequence).

These sequences are novel splice variants which results from alternative splicing of the original PSA sequence (this term according to the glossary refers also to the KLK-2 sequence).

The present invention further provides a protein or polypeptide comprising or consisting of an amino acid sequence encoded by any of the above nucleic acid sequences, termed herein "PSA variant product", for example, an amino acid sequence having the sequence as depicted in any one of SEQ ID NO: 7 to SEQ ID NO: 12 fragments of the above amino acid sequence having a length of at least 10 amino acids, in particular fragments comprising sequences which do not appear in the original PSA sequence, as well as homologues of the amino acid sequences SEQ ID NO:7 to SEQ ID NO: 12 in which one or more of the amino acid residues has been substituted (by conservative or non-conservative substitution) added, deleted, or chemically modified.

The novel PSA variant products of the invention may have the same physiological activity as the original PSA peptide (this term refers also to the KLK-2 product) from which they are varied (although perhaps at a different level); may have an opposite physiological activity from the activity featured by the original peptide from which they are varied; may have a completely different, unrelated activity to the activity of the original from which they are varied; or alternatively may have no activity at all and this may lead to various diseases or pathological conditions.

The novel variants of the invention whether being nucleic acid or amino acid sequences may serve for detection purposes, i.e. their presence or level may be indicative of prostate cancer, predisposition to prostate cancer, malignancy of the cancer, stage of the cancer, or may be indicative to normal condition. Alternatively the ratio between the level of each variant and the level original PSA sequence from which it has been varied; the ratio of each variant to the or other variants; the total amount (sum) of two or more variants either by itself or compared to other variants; or the sum of two or more variants, may be indicative of cancer or predisposition to cancer in general, and prostate cancer or predisposition to prostate cancer in particular, as well as indicative of the malignancy of the cancer, its stage of development or of normal condition. The variants may be detected in blood or serum or in the prostate gland, the ovary, breast or salivary glands, which may share gene properties with the prostate gland. The variant products may be soluble or membrane bound.

For example, for detection purposes, it is possible to establish differential expression of the various variants in various tissues. A certain variant may be expressed mainly in one tissue, while the original PSA sequence may be expressed mainly in another tissue such as the prostate. Understanding of the distribution of the variants in various tissues may be helpful in basic research, for understanding the physiological function of the genes as well as may help in targeting pharmaceuticals or developing pharmaceuticals.

The study of the variants may also be helpful to distinguish various stages in the life cycles of the same type of cells which may also be helpful for development of pharmaceuticals for various pathological conditions in which cell cycles is un-normal, notably cancer. For example, various stages in the development of prostate cancer may be characterized by expression, or change in level of individual PSA variants of the invention.

Thus the detection may by determination of the presence or the level of expression of the variant within a specific cell population, comprising said presence or level between various cell types in a tissue, between different tissues and between individuals.

The present invention further provides nucleic acid molecule comprising or consisting of a sequence which encodes the above amino acid sequences, (including the fragments and analogs of the amino acid sequences). Due to the degenerative nature of the genetic code, a plurality of alternative nucleic acid sequences, beyond those of SEQ ID NO:1 to SEQ ID NO: 6, can code for the amino acid sequences of the invention. Those alternative nucleic acid sequences which code for the amino acid sequences codes by any one of the sequence SEQ ID NO: 1 to SEQ ID NO: 6 are also an aspect of the of the present invention.

The present invention further provides expression vectors and cloning vectors comprising any of the above nucleic acid sequences, as well as host cells transfected by said vectors.

The present invention still further provides pharmaceutical compositions comprising, as an active ingredient, said nucleic acid molecules, said expression vectors, or said protein or polypeptide.

These pharmaceutical compositions are suitable for the treatment of diseases and pathological conditions, which can be ameliorated or cured by raising the level of the PSA variant product, for example for the treatment of prostate cancer, or for inhibiting the transformation from prostate hyperplasia to malignancy. By another aspect, the present invention provides a nucleic acid molecule comprising or consisting of a non-coding sequence which is complementary to that of any one of SEQ ID NO:1 to SEQ ID NO: 6, or complementary to a sequence having at least 90% identity to said sequence or a fragment of said two sequences. The complementary sequence may be a DNA sequence which hybridizes with any one of the SEQ of ID NO:1 to SEQ ID NO: 6 or hybridizes to a portion of that sequence having a length sufficient to inhibit the transcription of the complementary sequence. The complementary sequence may be a DNA sequence which can be transcribed into an mRNA being an antisense to the mRNA transcribed from SEQ ID NO:1 to SEQ ID NO: 6 or into an mRNA which is an antisense to a fragment of the mRNA transcribed from SEQ ID NO:1 to SEQ ID NO: 6 which has a length sufficient to hybridize with the mRNA transcribed from SEQ ID NO: 1 to SEQ ID NO:6, so as to inhibit its translation. The complementary sequence may also be the mRNA or the fragment of the mRNA itself.

The nucleic acids of the invention may be used for therapeutic or diagnostic applications for example for detection of the expression of PSA variant in various tissues which may be indicative to the presence of prostate cancer, indicative of pre-disposition to prostate cancer, as well as indicative of the malignancy and hence the prognosis of the prostate cancer. The variants of the invention may also be indicative of other types of cancer from glands binding physiological similarity to the prostate gland such as ovary, breast, and salivary gland.

The present invention also provides expression vectors comprising any one of the above defined complementary nucleic acid sequences and host cells transfected with said nucleic acid sequences or vectors, being complementary to those specified in the first aspect of the invention.

The invention also provides anti-PSA variant product antibodies, namely antibodies directed against the PSA variant product which specifically bind to said PSA variant product. Said antibodies are useful both for diagnostic and therapeutic purposes. For example said antibody may be used to detect the presence of prostate specific antigen-variant product in various tissues which may be indicative of the presence of prostate cancer of a predisposition for having prostate cancer, or of the malignancy of prostate cancer.

The present invention further concerns distinguishing antibodies which can bind only to a sequence present in the variants of the invention which is not present (as a continuous sequence) in the original PSA sequence. The present invention further concerns amino acid sequences for producing said distinguishing antibodies termed "distinguishing amino acid sequences" which are sequences present in the novel PSA variant and not present (as a continuous sequence) in the original PSA. An example of such a sequence is the sequence of positions 33–51 in SEQ ID NO:7 being:

Cys-Gln-Ala-Glu-Leu-Ser-Pro-Pro-Thr-Gln-His-Pro-Ser-Pro-Asp-Arg-Glu-Leu

The present invention also provides pharmaceutical compositions comprising, as an active ingredient, the nucleic acid molecules which comprise or consist of said complementary sequences, or of a vector comprising said complementary sequences. Alternatively, the pharmaceutical composition can comprise, as an active ingredient, said anti-PSA variant product antibodies, or said distinguishing antibodies.

The pharmaceutical compositions comprising said anti-PSA variant product antibodies, said distinguishing antibodies or the nucleic acid molecule comprising said complementary sequence, are suitable for the treatment of diseases and pathological conditions where a therapeutically beneficial effect may be achieved by neutralizing at least one of the PSA variants or decreasing the amount of the PSA variant product or blocking its binding to the receptor, for example, by the neutralizing effect of the antibodies, or by the effect of the antisense mRNA in decreasing expression level of the PSA variant product. An example of such a disease is prostate cancer. Furthermore, where the PSA variant is membrane bound, the anti-PSA variant antibodies may be used to target cytotoxic or cytostatic compounds to the tumor cells, in particular to prostate tumor cells. Since PSA variants may be produced specifically by prostate tumor cells, (and not normal prostate cells) and since this protein may be membrane associated, conjugates of anti-PSA variant antibodies and a drug can be targeted only to tumor cells and not harm healthy cells.

According to the third aspect of the invention the present invention provides methods for detecting the level of the transcript (mRNA) of said PSA variant product in a body fluid sample, or in a specific tissue sample, for example by use of probes comprising or consisting of said sequences (which may be a coding or uncoding sequence), as well as methods for detecting levels of expression of said product in tissue, e.g. by the use of antibodies capable of specifically reacting with the above amino acid sequences.

The method, according to this latter aspect, for detection of a nucleic acid sequence which encodes the PSA variant product in a biological sample, comprises the steps of:

(a) providing a probe comprising at least one of the nucleic acid sequence defined above;

(b) contacting the biological sample with said probe under conditions allowing hybridization of nucleic acid sequences thereby enabling formation of hybridization complexes;

(c) detecting hybridization complexes, wherein the presence of the complex indicates the presence of nucleic acid sequence encoding the PSA variant product in the biological sample.

The method as described above is qualitative, i.e. indicates whether the transcript is present in or absent from the sample. The method can also be quantitative, by determining the level of hybridization complexes and then calibrating said levels to determining levels of transcripts of the desired PSA variant in the sample.

Both qualitative and quantitative determination methods can be used for diagnostic, prognostic and therapy planning purposes.

By a preferred embodiment the probe is part of a nucleic acid chip used for detection purposes, i.e. the probe is a part of an array of probes each present in a known location on a solid support.

As indicated above the method may be utilized for detecting the presence of prostate cancer, detecting predisposition to prostate cancer, or evaluating the malignancy of prostate cancer, or assessing the development stage of the cancer.

The nucleic acid sequence used in the above method may be a DNA sequence, an RNA sequence, etc; it may be a coding or a sequence, or a non-coding sequence, or a sequence complementary thereto (for respective detection of RNA transcripts or coding-DNA sequences). By quantization of the level of hybridization complexes and calibrating the quantified results it is possible also to detect the level of the transcript in the sample.

The probes of the invention may be used to detect polymorphisms (in a specific individual or while screening a population) specifically for pre-disposition to cancer (especially prostate cancer) and loss-of-heterozigosity may be important for monitoring the development of the disease. Detection of disease predisposition or loss of heterozigosity in prostate tissue may be performed on either the coding or non-coding DNA sequence. One example of such a test is the determination of the exact sequence before position 5620 in GenBank HUMPSANTIG/1257 of SEQ ID 1 5620 (which is non coding and which contains an additional inserted A as compared to the native PSA), or testing a possible A to G substitution in position 5573 of HUMPSANTIG/1210 of SEQ ID 1. Both these sites may be indicative of cancer risk and useful in prognosis.

Methods for detecting mutations in the region coding for the PSA variant product are also provided, which may be methods carried-out in a binary fashion, namely merely detecting whether there is any mismatches between the normal PSA variant nucleic acid sequence and the one present in the sample, or carried-out by specifically detecting the nature and location of the mutation.

The present invention also concerns a method for detecting PSA variant product in a biological sample, comprising the steps of:
  (a) contacting with said biological sample the antibody of the invention, thereby forming an antibody-antigen complex; and
  (b) detecting said antibody-antigen complex wherein the presence of said antibody-antigen complex correlates with the presence of PSA variant product in said biological sample.

As indicated above, the method can be quantitized to determine the level or the amount of the PSA variant in the sample, alone or in comparison to the level of the original PSA amino acid sequence from which it was varied, and qualitative and quantitative results may be used for diagnostic, prognostic and therapy planning purposes.

By yet another aspect the invention also provides a method for identifying candidate compounds capable of binding to the PSA variant product and modulating its activity (being either activators or deactivators). The method includes:
  (i) providing a protein or polypeptide comprising an amino acid sequence substantially as depicted in any one of SEQ ID NO: 7 to SEQ ID NO: 12, or a fragment of such a sequence;
  (ii) contacting a candidate compound with said amino acid sequence;
  (iii) measuring the physiological effect of said candidate compound on the activity of the amino acid sequences and selecting those compounds which show a significant effect on said physiological activity.

The activity of the amino acid which should be changed by the modulator (being either the activator or deactivator) may be for example the binding of the amino acid (PSA variant product) to its native, receptor. Any modulator which changes such an activity has an intersecting potential The present invention also concerns compounds identified by the above methods described above, which compound may either be an activator of the serotonin-receptor like product or a deactivator thereof.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows the sequence of the original PSA as depicted in HUMPSANTIG (SEQ ID NO: 13). (This is the genomic sequence, which is the same in PSA and PSAL);

FIG. 2 (SEQ ID NO: 14) shows the translation of the original PSA sequence;

FIG. 3 shows multiple alignment between the original PSA sequence (termed "SEQ ID NO: 14") and polypeptides (SEQ ID NOS: 7–11)respectively encoded by the sequences of the invention (PSAL-O is SEQ ID NO:1; PSAL-1 is SEQ ID NO:2, PSAL-2 is SEQ ID NO:3; PSAL-5 is SEQ ID NO:4 and PSAL-6 is SEQ ID NO:5);

FIG. 4 shows a multiple alignment between the 5 PSA splice variant products (SEQ ID NOS: 7–11) encoded by SEQ ID NOS: 1–5, respectively, as described in FIG. 3, and the direct translation of the genomic PSA region, depicted here as HUMPSANTIG (SEQ ID NO: 13);

FIG. 5 shows the specific region (signal peptide SEQ ID NO: 15) of the original KLK-2 (Accession No: NM 005551) that is common with the splice variant of KLK-2 (SEQ ID NO: 12);

FIG. 7 shows a Northern Plot analysis of RNA obtained from various tissues and tested with probes for PSA (left) and probes obtained from SEQ ID NO:2, (termed PSALM in the Figure) (right);

FIG. 8 shows a Western Blot analysis of proteins obtained from prostate glands of several patients tested for PSA protein (left) and the PSA variant protein depicted in SEQ ID NO: 7 (right);

FIG. 9 shows immuno-histochemical labeling of human prostate gland with serum of rabbit immunized with PSAL variant peptide of the invention corresponding to SEQ ID NO: 7 (right) or unimmunized rabbit;

FIG. 10 shows a cross-section of in-situ hybridization of sense and anti-sense probes of PSA (termed "PSALM")

Figure 6:
FIG. 6 shows a schematic representation of the common locus of the KLK-2 of PSA genes.
Figure 11:
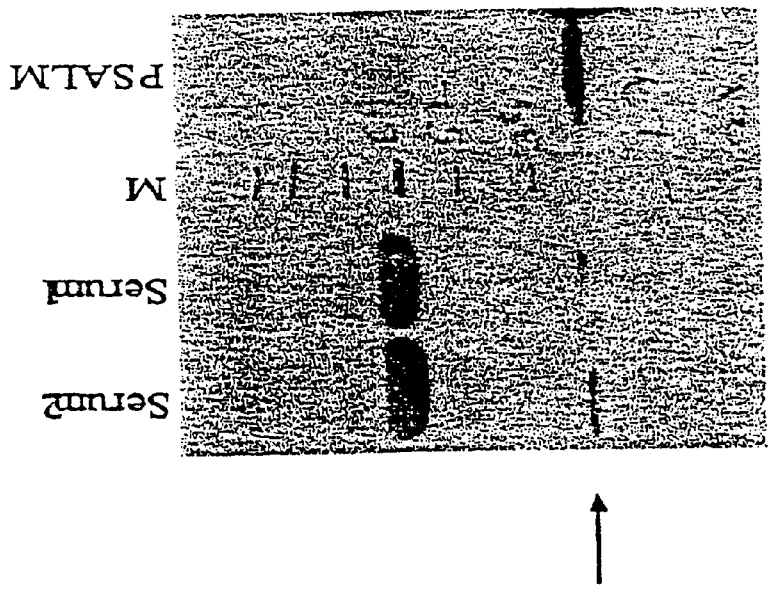
Figure 13:
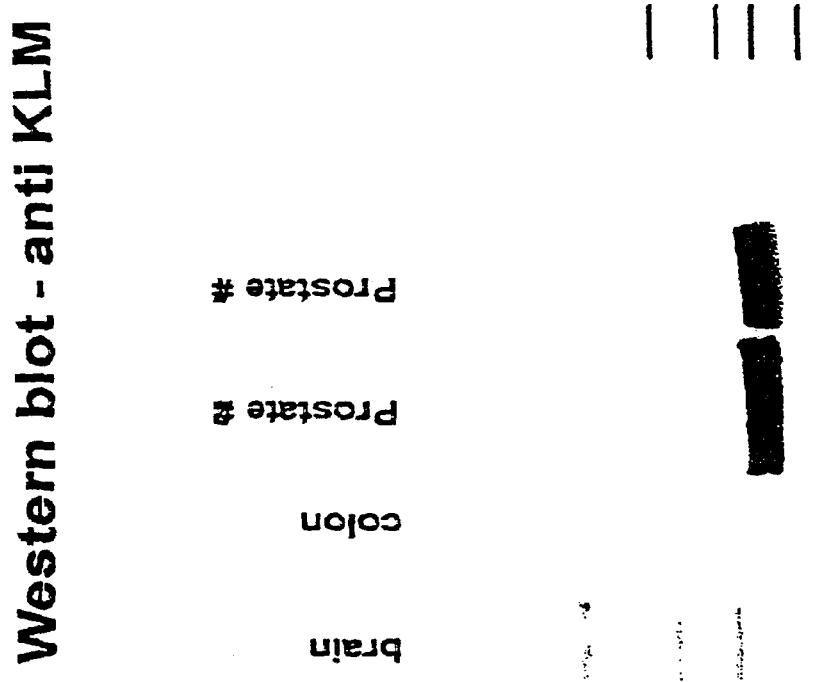

derived from sequence depicted as SEQ ID NO: 2 to tissue obtained from a prostate cancer;

FIG. 11 shows a Western blot analysis of 2 different serum-samples tested for PSA protein PSA (termed "PSALM"). The results indicate that the PSA is secreted to the serum. In the right lane there is a recombinant PSA corresponding to SEQ ID NO: 7;

FIG. 12 shows immuno-histochemical labeling of human prostate gland with serum of rabbit immunized with the peptide of the invention (derived from alternative splicing of the KLK-2 gene) (right) or unimmunized rabbit; and FIG. 13 shows a Western blot analysis of proteins obtained from prostate glands of 2 different patients (prostate #1 and #2), and from other tissues tested for the protein of the invention derived from the KLK-2 gene.

DETAILED DESCRIPTION OF A PREFERRED EMBODIMENT

EXAMPLE I

PSA Variant—Nucleic Acid Sequence

The nucleic acid sequences of the invention include nucleic acid sequences which encode PSA variant product and fragments and analogs thereof. The nucleic acid sequences may alternatively be sequences complementary to the above coding sequence, or to a region of said coding sequence. The length of the complementary sequence is sufficient to avoid the expression of the coding sequence. The nucleic acid sequences may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand. The nucleic acid sequences may also both include dNTPs, rNTPs as well as non naturally occurring sequences. The sequence may also be a part of a hybrid between an amino acid sequence and a nucleic acid sequence.

In a general embodiment, the nucleic acid sequence has at least 70%, preferably 80% or 90% sequence identity with the sequence identified as SEQ ID NO:1 to SEQ ID NO:6.

The nucleic acid sequences may include the coding sequence by itself. By another alternative the coding region may be in combination with additional coding sequences, such as those coding for fusion protein or signal peptides, in combination with non-coding sequences, such as introns and control elements, promoter and terminator elements or 5' and/or 3' untranslated regions, effective for expression of the coding sequence in a suitable host, and/or in a vector or host environment in which the PSA variant nucleic acid sequence is introduced as a heterologous sequence.

The nucleic acid sequences of the present invention may also have the product coding sequence fused in-frame to a marker sequence which allows for purification of the PSA variant product. The marker sequence may be, for example, a hexahistidine tag to provide for purification of the mature polypeptide fused to the marker in the case of a bacterial host, or, the marker sequence may be a hemagglutinin (HA) tag when a mammalian host, e.g. COS-7 cells, is used. The HA tag corresponds to an epitope derived from the influenza hemagglutinin protein (Wilson, I., et al. Cell 37:767 (1984)).

Also included in the scope of the invention are fragments also referred to herein as oligonucleotides, typically having at least 20 bases, preferably 20–30 bases corresponding to a region of the coding-sequence nucleic acid sequence. The fragments may be used as probes, primers, and when complementary also as antisense agents, and the like, according to known methods.

As indicated above, the nucleic acid sequence may be substantially a depicted in SEQ ID NO:1 to SEQ ID NO:6 or fragments thereof or sequences having at least 70%, preferably 70–80%, most preferably 90% identity to the above sequence. Alternatively, due to the degenerative nature of the genetic code, the sequence may be a sequence coding the amino acid sequence of SEQ ID NO:6 to SEQ ID NO:12, or fragments or analogs of said amino acid sequence.

A. Preparation of Nucleic Acid Sequences

The nucleic acid sequences may be obtained by screening cDNA libraries using oligonucleotide probes which can hybridize to or PCR-amplify nucleic acid sequences which encode the PSA variant products disclosed above. cDNA libraries prepared from a variety of tissues are commercially available and procedures for screening and isolating cDNA clones are well-known to those of skill in the art. Such techniques are described in, for example, Sambrook et al. (1989) Molecular Cloning: A Laboratory Manual (2nd Edition), Cold Spring Harbor Press, Plainview, N.Y. and Ausubel F M et al. (1989) Current Protocols in Molecular Biology, John Wiley & Sons, New York, N.Y.

The nucleic acid sequences may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the PACE method using, for example, the MARATHON PACE kit (Clontech, Cat. #K1802-1).

Alternatively, the technique of "restriction-site" PCR (Gobinda et al. PCR Methods Applic. 2:318–22, (1993)), which uses universal primers to retrieve flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia, T. et al., Nucleic Acids Res. 16:8186, (1988)). The primers may be designed using OLIGO(R) 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Capture PCR (Lagerstrom, M. et al., PCR Methods Applic. 1:111–19, (1991)) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker. J. D., et al., Nucleic Acids Res., 19:3055–60, (1991)). Additionally, one can use PCR, nested primers and PromoterFinder™ libraries to "walk in" genomic DNA (PromoterFinder™; Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes.

A randomly primed library may be particularly useful if an oligo d(T) library does not yield a full-length cDNA. Genomic libraries are useful for extension into the 5' non-translated regulatory region.

The nucleic acid sequences and oligonucleotides of the invention can also be prepared by solid-phase methods, according to known synthetic methods. Typically, fragments of up to about 100 bases are individually synthesized, then joined to form continuous sequences up to several hundred bases.

B. Use of PSA Variant Nucleic Acid Sequence for the Production of PSA Variant Products In accordance with the present invention, nucleic acid sequences specified above may be used as recombinant DNA molecules that direct the expression of PSA variant products.

As will be understood by those of skill in the art, it may be advantageous to produce PSA variant product-encoding nucleotide sequences possessing codons other than those which appear in any one of SEQ ID NO:1 to SEQ ID NO:6 which are those which naturally occur in the human genome. Codons preferred by a particular prokaryotic or eukaryotic host (Murray, E. et al. *Nuc Acids Res.*, 17:477–508, (1989)) can be selected, for example, to increase the rate of PSA variant product expression or to produce recombinant RNA transcripts having desirable properties, such as a longer half-life, than transcripts produced from naturally occurring sequence.

The nucleic acid sequences of the present invention can be engineered in order to alter a PSA variant product coding sequence for a variety of reasons, including but not limited to, alterations which modify the cloning, processing and/or expression of the product. For example, alterations may be introduced using techniques which are well known in the art, e.g., site-directed mutagenesis, to insert new restriction sites, to alter glycosylation patterns, to change codon preference, to produce splice variant, etc.

The present invention also includes recombinant constructs comprising one or more of the sequences as broadly described above. The constructs comprise a vector, such as a plasmid or viral vector, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells which are genetically engineered with vectors of the invention, and the production of the product of the invention by recombinant techniques. Host cells are genetically engineered (i.e., transduced, transformed or transfected) with the vectors of this invention which may be, for example, cloning vectors or expression vectors. The vector may be, for example, in the form of a plasmid, a viral particle, a phage, etc. The engineered host cells can be cultured in conventional nutrient media modified as appropriate for activating promoters, selecting transformants or amplifying the expression of the PSA variant nucleic acid sequence. The culture conditions, such as temperature, pH and the like, are those previously used with the host cell selected for expression, and will be apparent to those skilled in the art.

The nucleic acid sequences of the present invention may be included in any one of a variety of expression vectors for expressing a product. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: LTR or SV40 promoter, the *E.coli* Lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E.coli*.

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli*, Streptomyces, *Salmonella typhimurium*; fungal cells, such as yeast; insect cells such as Drosophila and Spodoptera Sf9; animal cells such as CHO, COS, HEK 293 or Bowes melanoma; adenoviruses; plant cells, etc. The selection of an appropriate host is deemed to be within the scope of those skilled in the art from the teachings herein. The invention is not limited by the host cells employed.

In bacterial systems, a number of expression vectors may be selected depending upon the use intended for the PSA variant product. For example, when large quantities of PSA variant product are needed for the induction of antibodies, vectors which direct high level expression of fusion proteins that are readily purified may be desirable. Such vectors include, but are not limited to, multifunctional *E. coli* cloning and expression vectors such as BLUESCRIPT(R) (Stratagene), in which the PSA variant polypeptide coding sequence may be ligated into the vector in-frame with sequences for the amino-terminal Met and the subsequent 7 residues of beta-galactosidase so that a hybrid protein is produced; pIN vectors (Van Heeke & Schuster J. Biol. Chem. 264:5503–5509, (1989)); PET vectors (Novagen, Madison Wis.); and the like.

In the yeast *Saccharomyces cerevisiae* a number of vectors containing constitutive or inducible promoters such as alpha factor, alcohol oxidase and PGH may be used. For reviews, see Ausubel et al. (supra) and Grant et al., (*Methods in Enzymology* 153:516–544, (1987)).

In cases where plant expression vectors are used, the expression of a sequence encoding PSA variant product may be driven by any of a number of promoters. For example, viral promoters such as the 35S and 19S promoters of CaMV (Brisson et al., *Nature* 310:511–514. (1984)) may be used alone or in combination with the omega leader sequence from TMV (Takamatsu et al., *EMBO J.*, 6:307–311, (1987)). Alternatively, plant promoters such as the small subunit of RUBISCO (Coruzzi et al., *EMBO J.* 3:1671–1680, (1984); Broglie et al., *Science* 224:838–843, (1984)); or heat shock promoters (Winter J and Sinibaldi R. M., *Results Probl. Cell Differ.*, 17:85–105, (1991)) may be used. These constructs can be introduced into plant cells by direct DNA transformation or pathogen-mediated transfection. For reviews of such techniques, see Hobbs S. or Murry L. E. (1992) in McGraw Hill Yearbook of Science and Technology, McGraw Hill, New York, N.Y., pp 191–196; or Weissbach and Weissbach (1988) *Methods for Plant Molecular Biology*, Academic Press, New York, N.Y., pp 421–463.

PSA variant product may also be expressed in an insect system. In one such system, Autographa californica nuclear polyhedrosis virus (AcNPV) is used as a vector to express foreign genes in *Spodoptera frugiperda* cells or in Trichoplusia larvae. The PSA variant product coding sequence may be cloned into a nonessential region of the virus, such as the polyhedrin gene, and placed under control of the polyhedrin promoter. Successful insertion of PSA variant coding sequence will render the polyhedrin gene inactive and produce recombinant virus lacking coat protein coat. The recombinant viruses are then used to infect *S. frugiperda* cells or Trichoplusia larvae in which PSA variant protein is expressed (Smith et al., *J. Virol.* 46:584, (1983); Engelhard, E. K. et al., *Proc. Nat. Acad. Sci.* 91:3224–7, (1994)).

In mammalian host cells, a number of viral-based expression systems may be utilized. In cases where an adenovirus is used as an expression vector, a PSA variant product coding sequence may be ligated into an adenovirus transcription/translation complex consisting of the late promoter and tripartite leader sequence. Insertion in a nonessential E1 or E3 region of the viral genome will result in a viable virus capable of expressing PSA variant protein in infected host cells (Logan and Shenk, *Proc. Natl. Acad. Sci.* 81:3655–59, (1984). In addition, transcription enhancers, such as the Rous sarcoma virus (RSV) enhancer, may be used to increase expression in mammalian host cells.

Specific initiation signals may also be required for efficient translation of a PSA variant protein coding sequence. These signals include the ATG initiation codon and adjacent sequences. In cases where PSA variant product coding sequence, its initiation codon and upstream sequences are inserted into the appropriate expression vector, no additional translational control signals may be needed. However, in cases where only coding sequence, or a portion thereof, is inserted. exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D. et al., (1994) *Results Probl. Cell Differ.,* 20:125–62, (1994); Bittner et al., *Methods in Enzymol* 153:516–544, (1987)).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology). Cell-free translation systems can also be employed to produce polypeptides using RNAs derived from the DNA constructs of the present invention.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre-pro" form of the protein may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express PSA variant product may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M., et al., *Cell* 11:223–32, (1977)) and adenine phosphoribosyltransferase (Lowy I., et al., *Cell* 22:817–23, (1980)) genes which can be employed in tk- or aprt-cells, respectively. Also, antimetabolite, antibiotic or herbicide resistance can be used as the basis for selection; for example, dhfr which confers resistance to methotrexate (Wigler M., et al., *Proc. Natl. Acad. Sci.* 77:3567–70, (1980)); npt, which confers resistance to the aminoglycosides neomycin and G-418 (Colbere-Garapin, F. et al., *J. Mol. Biol.,* 150:1–14, (1981)) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan, *Proc. Natl. Acad. Sci.* 85:8047–51, (1988)). The use of visible markers has gained popularity with such markers as anthocyanins, beta-glucuronidase and its substrate, GUS, and luciferase and its substrates, luciferin and ATP, being widely used not only to identify transformants, but also to quantify the amount of transient or stable protein expression attributable to a specific vector system (Rhodes, C. A. et. al., *Methods Mol. Biol.,* 55:121–131, (1995)).

Host cells transformed with a nucleotide sequence encoding PSA variant product may be cultured under conditions suitable for the expression and recovery of the encoded protein from cell culture. The product produced by a recombinant cell may be secreted or contained intracellularly depending on the sequence and/or the vector used. As will be understood by those of skill in the art, expression vectors containing nucleic acid sequences encoding PSA variant product can be designed with signal sequences which direct secretion of PSA variant product through a prokaryotic or eukaryotic cell membrane.

PSA variant product may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and PSA variant protein is useful to facilitate purification.

One such expression vector provides for expression of a fusion protein compromising a PSA variant polypeptide fused to a polyhistidine region separated by an enterokinase cleavage site. The histidine residues facilitate purification on IMIAC (immobilized metal ion affinity chromatography, as described in Porath, et al., *Protein Expression and Purification*, 3:263–281, (1992)) while the enterokinase cleavage site provides a means for isolating PSA variant polypeptide from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

The PSA variant products can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

C. Diagnostic Applications Utilizing Nucleic Acid Sequences

The nucleic acid sequences of the present invention may be used for a variety of diagnostic purposes. The nucleic acid sequences may be used to detect and quantitate expression of PSA variant in patient's cells, e.g. biopsied tissues, by detecting the presence of mRNA coding for PSA variant product. Alternatively, the assay may be used to detect free PSA variant in the serum or blood. This assay typically involves obtaining total mRNA from the tissue or serum and contacting the mRNA with a nucleic acid probe. The probe is a nucleic acid molecule of at least 20 nucleotides, preferably 20–30 nucleotides, capable of specifically hybridizing with a sequence included within the sequence of a nucleic acid molecule encoding PSA variant under hybridizing conditions, detecting the presence of mRNA hybridized to the probe, and thereby detecting the expression of PSA variant. This assay can be used to distinguish between absence, presence, and excess expression of PSA variant product and to monitor levels of PSA variant expression during therapeutic intervention.

The invention also contemplates the use of the nucleic acid sequences as a diagnostic for diseases resulting from inherited defective PSA variant sequences. These sequences can be detected by comparing the sequences of the defective (i.e., mutant) PSA variant coding region with that of a normal coding region. Association of the sequence coding for mutant PSA variant product with abnormal PSA variant product activity may be verified. In addition, sequences encoding mutant PSA variant products can be inserted into a suitable vector for expression in a functional assay system (e.g., colorimetric assay, complementation experiments in a PSA variant protein deficient strain of HEK293 cells) as yet another means to verify or identify mutations. Once mutant genes have been identified, one can then screen populations of interest for carriers of the mutant gene.

Individuals carrying mutations in the nucleic acid sequence of the present invention may be detected at the DNA level by a variety of techniques. Nucleic acids used for diagnosis may be obtained from a patient's cells, including but not limited to such as from blood, urine, saliva, placenta, tissue biopsy and autopsy material and in particular tissue obtained from the prostate gland. Genomic DNA may be used directly for detection or may be amplified enzymatically by using PCR (Saiki, et al., *Nature* 324:163–166, (1986)) prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and S1 protection or the chemical cleavage method (e.g. Cotton, et al *Proc. Natl. Acad. Sci. USA*, 85:4397–4401, (1985)), or by differences in melting temperatures. "*Molecular beacons*" (Kostrikis L. G. et al., *Science* 279:1228–1229, (1998)), hairpin-shaped, single-stranded synthetic oligo-nucleotides containing probe sequences which are complementary to the nucleic acid of the present invention, may also be used to detect point mutations or other sequence changes as well as monitor expression levels of PSA variant product.

Another method for detecting mutations uses two DNA probes which are designed to hybridize to adjacent regions of a target, with abutting bases, where the region of known or suspected mutation(s) is at or near the abutting bases. The two probes may be joined at the abutting bases, e.g., in the presence of a ligase enzyme, but only if both probes are correctly base paired in the region of probe junction. The presence or absence of mutations is then detectable by the presence or absence of ligated probe.

Also suitable for detecting mutations in the PSA variant product coding sequence are oligonucleotide array methods based on sequencing by hybridization (SBH), as described, for example, in U.S. Pat. No. 5,547,839. In a typical method, the DNA target analyte is hybridized with an array of oligonucleotides formed on a microchip. The sequence of the target can then be "read" from the pattern of target binding to the array.

D. In situ Hybridization Using Probes of PSA

In-situ hybridisation was carried out according to the procedure described in the Boehringer-Mannheim's publication "Non-Radioative In-Situ Hybridization Application Manual", $2^{nd}$ edition, 1996. Labelling was carried out according to Chapter 4, section V, and hybridization according to Chapter 5, section IV. Slides were prepared in paraffin and treated according to the procedures described in Chapter 2. The probe used was derived from the PSAL-1 sequence (SEQ ID NO: 2). The anti-sense probe was used to detect the presence of PSA variant mRNA, and the sense probe was used as control. Results in FIG. 10 indicates high-level expression of the PSA variant mRNA in prostate epithelial lumen cells.

E. Therapeutic Applications of Nucleic Acid Sequences

Nucleic acid sequences of the invention may also be used for therapeutic purposes. Turning first to the anti-PSA variant aspect, expression of PSA variant product may be modulated through antisense technology, which controls gene expression through hybridization of complementary nucleic acid sequences, i.e. antisense DNA or RNA, to the control, 5' or regulatory regions of the gene encoding PSA variant product. For example, the 5' coding portion of the nucleic acid sequence sequence which codes for the product of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the nucleic acid sequence involved in transcription (Lee et al., *Nucl. Acids, Res.*, 6:3073, (1979); Cooney et al., *Science* 241:456, (1988); and Dervan et al., *Science* 251:1360, (1991)), thereby preventing transcription and the production of the PSA variant products. An antisense RNA oligonucleotide hybridizes to the mRNA in vivo and blocks translation of the mRNA molecule into the PSA variant products (Okano *J. Neurochem.* 56:560, (1991)). The antisense constructs can be delivered to cells by procedures known in the art such that the antisense RNA or DNA may be expressed in vivo. The antisense may be antisense mRNA or DNA sequence capable of coding such antisense mRNA. The antisense mRNA or the DNA coding thereof can be complementary to the full sequence of nucleic acid sequences coding to the PSA variant protein or to a fragment of such a sequence which is sufficient to inhibit production of a protein product.

Turning now to the PSA variant aspect, expression of PSA variant product may be increased by providing coding sequences for coding for said product under the control of suitable control elements ending its expression in the desired host.

The nucleic acid sequences of the invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The polypeptides, and activator and deactivator compounds (see below), which are polypeptides, may also be employed in accordance with the present invention by expression of such polypeptides in vivo, which is often referred to as "gene therapy." Cells from a patient may be engineered with a nucleic acid sequence (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a product of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, psi-2, psi-AM, PA12, T19-14X, VT-19-17-H2, psi-CRE, psi-CRIP, GP+E-86, GP+envAm12, and DAN cell lines as described in Miller (*Human Gene Therapy*, Vol. 1, pg. 5–14, (1990)). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The genes introduced into cells may be placed under the control of inducible promoters, such as the radiation-inducible Egr-1 promoter, (Maceri, H. J., et al., *Cancer Res.*, 56(19):4311 (1996)), to stimulate PSA variant production or antisense inhibition in response to radiation, eg., radiation therapy for treating tumors.

F. Northern Blot Analysis

RNA samples were obtained from spleen, thymus, prostate, testis, ovary, small intestine, colon and leukocytes electrophoresed through a 1.5% agarose gel containing formaldehyde and transfered onto nylon HYBOND, Amersham) paper (Thomas, 1980). Prehybridization was for 2 hours in a buffer containing 10% Dextrane Sulfate, 1M NaCl and 1% SDS, at 65° C. Hybridization was in the same buffer with 5×106 cpm of the appropriate probe at 65° C. for 18 hours. After one wash in 2×SSC, 0.1% SDS for 15 minutes at 65° C. and several washes in 0.2×SSC, 0.1% SDS at 65° C. the filter was exposed to an X-ray film. Phosphorimager analysis was performed as well. The results are shown in FIG. 7. As can be seen with the PSA probe (left), a single band was detected, while with the probe of the invention (termed "PSAL") (derived from SEQ ID 2, in the common region with SEQ IDs 3, 4, and 5) several bands were detected in prostate tissue, which indicates the presence of different PSA splice variants.

EXAMPLE II

PSA Variant Product

The substantially purified PSA variant product of the invention has been defined above as the product coded from the nucleic acid sequence of the invention. Preferably the amino acid sequence is an amino acid sequence having at least 90% identity to the sequence identified as any one of SEQ ID NO:7 to SEQ. ID NO. 12. The protein may be in mature and/or modified form, also as defined above. Also contemplated are protein fragments having at least 10 contiguous amino acid residues, preferably at least 10–20 residues, derived from the PSA variant protein.

The sequence variations are preferably those that are considered conserved substitutions, as defined above. Thus, for example, a protein with a sequence having at least 80% sequence identity with the protein identified as SEQ ID NO:7 to SEQ ID NO: 12, preferably by utilizing conserved substitutions as defined above. In a more specific embodiment, the protein has or contains the sequence identified SEQ ID NO:7 to SEQ. ID NO: 12. The PSA variant product may be (i) one in which one or more of the amino acid residues in a sequence listed above are substituted with a conserved or non-conserved amino acid residue (preferably a conserved amino acid residue), or (ii) one in which one or more of the amino acid residues includes a substituent group, or (iii) one in which the PSA variant product is fused with another compound, such as a compound to increase the half-life of the protein (for example, polyethylene glycol (PEG)), or a moiety which serves as targeting means to direct the protein to its target tissue or target cell population (such as an antibody), or (iv) one in which additional amino acids are fused to the PSA variant product. Such fragments, variant and derivatives are deemed to be within the scope of those skilled in the art from the teachings herein.

A. Preparation of PSA Variant Product

Recombinant methods for producing and isolating the PSA variant product, and fragments of the protein are described above.

In addition to recombinant production, fragments and portions of PSA variant product may be produced by direct peptide synthesis using solid-phase techniques (cf. Stewart et al., (1969) Solid-Phase Peptide Synthesis, WH Freeman Co, San Francisco; Merrifield J., *J. Am. Chem. Soc.,* 85:2149–2154, (1963)). In vitro peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Fragments of PSA variant product may be chemically synthesized separately and combined using chemical methods to produce the fill length molecule.

B. Western Blot Analysis

Western Blot analysis was performed according to procedures well known in the art, that are described in the Maniatis Laboratory Manual. Post processing was performed using PIERCE SuperSignal staining kit.

CG-47, CG-30, CG-23, and CG-35 are all hyperplastic prostate tissue sample. CG-37 is a normal prostate sample. The results indicate that the original PSA is expressed in hyperplastic, but not normal, prostate tissue (right) while the PSA variant (denoted PSALM) is weakly present hyperplastic prostate and highly expressed in normal tissue. Neither molecule is present in detectable levels in the spleen control.

C. Therapeutic Uses and Compositions Utilizing the PSA Variant Product

The PSA variant product of the invention is generally useful in treating diseases and disorders which are characterized by a lower than normal level of PSA variant expression, and or diseases which can be cured or ameliorated by raising the level of the PSA variant product, even if the level is normal.

PSA variant products or fragments may be administered by any of a number of routes and methods designed to provide a consistent and predictable concentration of compound at the target organ or tissue. The product-containing compositions may be administered alone or in combination with other agents, such as stabilizing compounds, and/or in combination with other pharmaceutical agents such as drugs or hormones.

PSA variant product-containing compositions may be administered by a number of routes including, but not limited to oral, intravenous, intramuscular, transdermal, subcutaneous, topical, sublingual, or rectal means as well as by nasal application. PSA variant product-containing compositions may also be administered via liposomes. Such administration routes and appropriate formulations are generally known to those of skill in the art.

The product can be given via intravenous or intraperitoneal injection. Similarly, the product may be injected to other localized regions of the body. The product may also be administered via nasal insufflation. Enteral administration is also possible. For such administration, the product should be formulated into an appropriate capsule or elixir for oral administration, or into a suppository for rectal administration.

The foregoing exemplary administration modes will likely require that the product be formulated into an appropriate carrier, including ointments, gels, suppositories. Appropriate formulations are well known to persons skilled in the art.

Dosage of the product will vary, depending upon the potency and therapeutic index of the particular polypeptide selected.

A therapeutic composition for use in the treatment method can include the product in a sterile injectable solution, the polypeptide in an oral delivery vehicle, the product in an aerosol suitable for nasal administration, or the product in a nebulized form, all prepared according to well known methods. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof.

EXAMPLE III

Screening Methods for Activators and Deactivators

The present invention also includes an assay for identifying molecules, such as synthetic drugs, antibodies, peptides, or other molecules, which have a modulating effect on the activity of the PSA variant product, e.g. activators or deactivators of the PSA variant product of the present invention. Such an assay comprises the steps of providing an PSA variant product encoded by the nucleic acid sequences of the present invention, contacting the PSA variant protein with one or more candidate molecules to determine the candidate molecules modulating effect on the activity of the PSA variant product, and selecting from the molecules a candidate's molecule capable of modulating PSA variant product physiological activity.

PSA variant product, its catalytic or immunogenic fragments or oligopeptides thereof, can be used for screening therapeutic compounds in any of a variety of drug screening techniques. The fragment employed in such a test may be free in solution, affixed to a solid support, borne on a cell membrane or located intracellularly. The formation of binding complexes, between PSA variant product and the agent being tested, may be measured. Alternatively, the activator or deactivator may work by serving as agonist or antagonist, respectively, of the PSA variant receptor and their effect may be determined in connection with the receptor.

Another technique for drug screening which may be used provides for high throughput screening of compounds having suitable binding affinity to the PSA variant product is described in detail by Geysen in PCT Application WO 84/03564, published on Sep. 13, 1984. In summary, large numbers of different small peptide test compounds are synthesized on a solid substrate, such as plastic pins or some other surface. The peptide test compounds are reacted with the full PSA variant product or with fragments of PSA variant product and washed. Bound PSA variant product is then detected by methods well known in the art. Substantially purified PSA variant product can also be coated directly onto plates for use in the aforementioned drug screening techniques. Alternatively, non-neutralizing antibodies can be used to capture the peptide and immobilize it on a solid support.

Antibodies to the PSA variant product, as described in Example IV below, may also be used in screening assays according to methods well known in the art. For example, a "sandwich" assay may be performed, in which an anti-PSA variant antibody is affixed to a solid surface such as a microtiter plate and PSA variant product is added. Such an assay can be used to capture compounds which bind to the PSA variant product. Alternatively, such an assay may be used to measure the ability of compounds to influence with the binding of PSA variant product to the PSA variant receptor, and then select those compounds which effect the binding.

EXAMPLE IV
Anti-PSA Variant Antibodies
A. Synthesis

In still another aspect of the invention, the purified PSA variant product is used to produce anti-PSA variant antibodies which have diagnostic and therapeutic uses related to the activity, distribution, and expression of the PSA variant product, in particular diagnostic application in identification of prostate cancer, (distinguishing between malignant and benign states) and as targeting means for delivery of cytotoxic compounds to tumor cells.

Antibodies to PSA variant product may be generated by methods well known in the art. Such antibodies may include, but are not limited to, polyclonal, monoclonal, chimeric, humanized, single chain, Fab fragments and fragments produced by an Fab expression library. Antibodies, i.e., those which inhibit dimer formation, are especially preferred for therapeutic use.

PSA variant product for antibody induction does not require biological activity; however, the protein fragment or oligopeptide must be antigenic. Peptides used to induce specific antibodies may have an amino acid sequence consisting of at least five amino acids, preferably at least 10 amino acids of the sequences specified in any of the 7 to 12 SEQ ID NO. Preferably they should mimic a portion of the amino acid sequence of the natural protein and may contain the entire amino acid sequence of a small, naturally occurring molecule. The antibodies may also distinguish antibodies, i.e. antibodies which bind to an amino acid sequence present in the PSA variant and not in the original PSA sequence. For the production of said distinguishing antibodies "distinguishing amino acid sequences" may be used for example having the sequence CQAEL-SPPTQHPSPDREL (SEQ ID NO: 16).

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci.* 86:3833–3837, 1989)), and Winter G and Milstein C., (*Nature* 349:293–299, (1991)).

Antibody fragments which contain specific binding sites for PSA variant protein may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W. D. et al., *Science* 256:1275–1281, (1989)).

Production of Antibodies

Human and mouse cDNA fragments were subcloned into the pET-28(a-c) vectors (Novagen,USA). DNA was prepared from positive clones and introduced into the *E.coli* strain DE3 according to the manufacturer's recommendations.After induction, extracts were electrophoresed through a 10% SDS-PAGE. Extracts were prepared from clones that expressed the expected size protein and loaded on a nickel-agarose column. The His containing proteins were isolated from the column according to the manufacturer's recommendations and used in injections. Polyclonal antibodies against human PSAL peptide were prepared by immunizing rabbits with 3–4 injections of 0.5 mg of the purified protein at 1–2 week intervals. Animals were bled 10 days after the final booster. Serum was separated from the blood and stored at −80 C. The peptide defined above as "distinguishing amino acid sequence" was used for immunization.

B. Diagnostic Applications of Antibodies

A variety of protocols for competitive binding or immunoradiometric assays using either polyclonal or monoclonal antibodies with established specificities are well known in the art. Such immunoassays typically involve the formation of complexes between PSA variant product and its specific antibody and the measurement of complex formation. A two-site, monoclonal-based immunoassay utilizing monoclonal antibodies reactive to two non-interfering epitopes on a specific PSA variant product is preferred, but a competitive binding assay may also be employed. These assays are described in Maddox D. E., et al., (J. Exp. Med. 158:1211, (1983)).

Antibodies which specifically bind PSA variant product are useful for the diagnosis of conditions or diseases characterized by expression of PSA variant protein, in particular prostate cancer. Alternatively, such antibodies may be used in assays to monitor patients being treated with PSA variant product, its activators, or its deactivators. Diagnostic assays for PSA variant protein include methods utilizing the antibody and a label to detect PSA variant product in human body fluids or extracts of cells or tissues. The products and antibodies of the present invention may be used with or without modification. Frequently, the proteins and antibodies will be labeled by joining them, either covalently or noncovalently, with a reporter molecule. A wide variety of reporter molecules are known in the art.

A variety of protocols for measuring PSA variant product, using either polyclonal or monoclonal antibodies specific for the respective protein are known in the art. Examples include enzyme-linked immunosorbent assay (ELISA), radioimmunoassay (RIA), and fluorescent activated cell sorting (FACS). As noted above, a two-site, monoclonal-based immunoassay utilizing monoclonal antibodies reactive to two non-interfering epitopes on PSA variant product is preferred, but a competitive binding assay may be employed. These assays are described, among other places, in Maddox, et al. (supra). Such protocols provide a basis for diagnosing altered or abnormal levels of PSA variant product expression. Normal or standard values for PSA variant product expression are established by combining body fluids or cell extracts taken from normal subjects, preferably human, with antibody to PSA variant product under conditions suitable for complex formation which are well known in the art. The amount of standard complex formation may be quantified by various methods, preferably by photometric methods. Then, standard values obtained from normal samples may be compared with values obtained from samples from subjects potentially affected by disease. Deviation between standard and subject values establishes the presence of disease state.

The antibody assays are useful to determine the level of PSA variant present in a body fluid sample, or in a particular tissue, e.g., biopsied tumor tissue, for example from the prostate gland, as an indication of whether PSA variant is being overexpressed or underexpressed in the tissue, or as an indication of how PSA variant levels are responding to drug treatment.

C. Immunohistochemical Staining

Human prostate micron sections were prepared using a R. Gung microtome and fixed on slides pretreated with 2% Tespa (Sigma, USA). Deparaffinization was performed for 30 minutes at 80° C. Hydration was executed by immersing the slides twice in xylene (5 minutes each), twice in 100% ethanol (5 minutes each), twice in 95% ethanol (5 minutes each), once in 70% ethanol (5 minutes), and once in PBS pH7.4 (10 minutes). After incubation in 50 µl/slide of 1.5 mg/ml hyaluronidase in PBS pH6.5 for 1 hour at 37° C. the slides were washed in PBS pH 7.4 (10 minutes). 50 µl/slide of 0.3% $H_2O_2$ in PBS pH 7.4 were added for 10 minutes after which they were washed in PBS pH 7.4 (10 minutes).

Blocking was performed by addition of 50 µl/slide of normal goat serum containing 20% trasylol at 37° C. for 10 minutes. Rabbit anti-testilin antibodies were diluted 1:50 in 10% blocking solution (normal goat serum containing 20% trasylol(Bayer, Germany) and interacted with the slides for 18 hours at 4° C.Then the slides were washed 3 times in PBS pH 7.4 and immersed for 10 minutes in PBS pH 7.4. Horse raddish peroxidase (HRP) conjugated goatanti rabbit antibodies (Sigma,USA) in PBS pH 7.4 containing 20% trasylol (Bayer, Germany) diluted 1:40, were added for 30 minutes at room temperature, in the dark, following by wash in PBS pH 7.4 for 10 minutes. For HRP reaction 0.4 mg/ml of the substrate (3'3' diaminbenzoidin) was added in the dark for 10 minutes. Following 3 washes in PBS pH 7.4 and immersion for 10 minutes in PBS pH 7.4, staining of the slides was performed with 1% methylene blue in PBS pH 7.4 for 5 mm. Following two washes in water, dehydration was carried out by immersing the slides 3 times in 70% ethanol, 3 times in 95% ethanol, 6 times in 100% ethanol and 6 times in xylene. Mounting was performed with MERCOGLASS (Merk, USA).The results are shown in FIG. 9. The result indicate a high presence level of the PSA variant protein in the lumen-lining of prostate epithelial cells (color gold, left picture, vs. the pre-immune serum control on the right picture, where no gold color is detectable.)

D. Therapeutic Uses of Antibodies

In addition to their diagnostic use the antibodies may have a therapeutical utility in blocking or decreasing the activity of the PSA variant product in pathological conditions where its activity or concentration are too high, for example in prostate cancer. In addition, the antibodies may be conjugated to cytotoxic compounds and thus may serve as means for targeting the cytotoxic moiety only to cancer cells which express membrane-bond PSA variant product.

The antibody employed is preferably a humanized monoclonal antibody, or a human Mab produced by known globulin-gene library methods. The antibody is administered typically as a sterile solution by IV injection, although other parenteral routes may be suitable. Typically, the antibody is administered in an amount between about 1–15 mg/kg body weight of the subject. Treatment is continued, e.g., with dosing every 1–7 days, until a therapeutic improvement is seen.

Although the invention has been described with reference to specific methods and embodiments, it is appreciated that various modifications and changes may be made without departing from the invention.

EXAMPLE V

Immuno-histochemistry

Immunohistochemical staining was performed using "HYSTOSTATINE SP" kit (Zymed Laboratories INC.).

Human prostate micron sections were prepared using a R. Gung microtome and fixed on superfrost slides with 2% Tespa. Deparaffinization was performed for 10 mins. at xylen. Hydration three times 100% ethanol and once 95% ethanol. The slides were washed in Ddw, following incubation with 3% $H_2O_2$ for 5 mins. After incubation the slides were washed twice in ddw, and twice in 0.05M Tris Hcl Ph 7.6 (optimax wash buffer, BioGenex).

Blocking was performed with serum blocking solution (ready to use, reagent A, Zymed) 100 ul each slide incubate 10 mins. Primary antibody was diluted 1:50 in antibody diluent reagent solution (Zymed), and incubated in moist chamber wit the slides for 1 hour.

Following washing (three times in optimax buffer) the slides were incubated with 100 µl biotinylated second antibody ready to use (reagent B Zymed), for 10 mins, then washed three more times in optimax buffer. The slides were incubated with 100 µl enzyme conjugate HRP-streptavidin ready to use (reagent C, Zymed) for 10 mins, and washed twice in optimax buffer. Then 100 µl substrate (liquid DAB substrate, Zymed) were added for 3 mins.

Following the incubation with the substrate, the slides were washed twice in ddw and stained with Hematoxylen solution (Zymed) for 2 mins. Then the slides were washed in tap water for 1 hour. The dehydration was carried out by immersing the slides 2 times in 95% ethanol, 3 times in 100% ethanol, 3 times in Zylen. Mounting was performed with mounting solution (Zymed).

The results are shown in FIG. 12. The results indicate a high presence level of the protein (derived by alternative splicing from the KLK-2 gene) in the lumen-lining of prostate epithelial cells (gold color, left picture, vs. the pre-immune serum control on the right picture, where no gold color is detectable).

What is claimed is:

1. An isolated nucleic acid sequence consisting of SEQ ID NO:6.

2. An isolated nucleic acid sequence fully complementary to the nucleic acid sequence of claim 1.

3. An isolated nucleic acid sequence encoding the amino acid sequence consisting of SEQ ID NO: 12.

4. An expression vector comprising the nucleic acid sequences of claim 1 or 3 and control elements for the expression of the nucleic acid sequence in a suitable host.

5. An expression vector comprising the nucleic acid sequence of claim 2, and control elements for the expression of the nucleic acid sequence in a suitable host.

6. An isolated host cell transfected by the expression vector of claim 4.

* * * * *